(12) United States Patent
Walsh et al.

(10) Patent No.: US 10,159,652 B2
(45) Date of Patent: Dec. 25, 2018

(54) DEVICE FOR FORMULATING PARTICLES AT SMALL VOLUMES

(71) Applicant: THE UNIVERSITY OF BRITISH COLUMBIA, Vancouver, British Columbia (CA)

(72) Inventors: Colin Walsh, Belmont, CA (US); Andre Wild, Vancouver (CA); Robert James Taylor, Vancouver (CA); Timothy Leaver, Delta (CA); Kevin Ou, Toronto (CA); Euan Ramsay, Vancouver (CA); Aysha Ansari, Calgary (CA)

(73) Assignee: The University of British Columbia, Vancouver (CA)

( * ) Notice: Subject to any disclaimer, the term of this patent is extended or adjusted under 35 U.S.C. 154(b) by 155 days.

(21) Appl. No.: 15/029,993

(22) PCT Filed: Oct. 16, 2014

(86) PCT No.: PCT/US2014/060961
§ 371 (c)(1),
(2) Date: Apr. 15, 2016

(87) PCT Pub. No.: WO2015/057998
PCT Pub. Date: Apr. 23, 2015

(65) Prior Publication Data
US 2016/0235688 A1    Aug. 18, 2016

Related U.S. Application Data

(60) Provisional application No. 61/891,758, filed on Oct. 16, 2013.

(51) Int. Cl.
*A61K 9/51* (2006.01)
*B01F 13/00* (2006.01)
(Continued)

(52) U.S. Cl.
CPC .......... *A61K 9/5192* (2013.01); *A61K 9/5123* (2013.01); *A61K 31/7105* (2013.01);
(Continued)

(58) Field of Classification Search
None
See application file for complete search history.

(56) References Cited

U.S. PATENT DOCUMENTS 5,417,956 A    5/1995 Moser
7,718,099 B2    5/2010 Kawai et al.
(Continued)

FOREIGN PATENT DOCUMENTS

CN        1612780 A    5/2005
CN    101523168 A    9/2009
(Continued)

OTHER PUBLICATIONS

Extended European Search Report dated Jul. 6, 2017, issued in corresponding European Application No. 14853947.1, filed Oct. 16, 2014, 7 pages.
(Continued)

*Primary Examiner* — Jeffrey D Washville
(74) *Attorney, Agent, or Firm* — Christensen O'Connor Johnson Kindness PLLC

(57) ABSTRACT

Methods and devices for making particles at small volumes.

14 Claims, 12 Drawing Sheets

A SCHEMATIC ILLUSTRATION OF THE CHALLENGES OF
MANUFACTURING PARTICLES AT SMALL VOLUMES

DEAD VOLUME CONTAINING WASTE FLUID EXISTS IN:
1) THE CONNECTIONS TO THE INPUTS;
2) THE INPUTS;
3) THE CHANNELS FROM THE INPUTS TO THE MIXER;
4) THE MIXER;
5) THE CHANNEL FROM THE MIXER TO THE OUTPUT.

(51) Int. Cl.
    *A61K 31/7105*     (2006.01)
    *B01F 3/08*     (2006.01)
    *B01F 5/02*     (2006.01)
    *B01F 13/10*     (2006.01)
    *B01J 2/06*     (2006.01)

(52) U.S. Cl.
    CPC .............. *B01F 3/08* (2013.01); *B01F 3/0807* (2013.01); *B01F 3/0811* (2013.01); *B01F 3/0861* (2013.01); *B01F 5/02* (2013.01); *B01F 13/0062* (2013.01); *B01F 13/1022* (2013.01); *B01J 2/06* (2013.01); *B01F 2215/0032* (2013.01)

(56) References Cited

U.S. PATENT DOCUMENTS

| | | |
|---|---|---|
| 2003/0201022 A1 | 10/2003 | Kawai et al. |
| 2004/0266892 A1 | 12/2004 | Nicola et al. |
| 2007/0242560 A1 | 10/2007 | Norikane et al. |
| 2010/0022680 A1* | 1/2010 | Karnik ................. A61K 9/5153 523/105 |
| 2010/0028236 A1 | 2/2010 | Shen et al. |

FOREIGN PATENT DOCUMENTS

| | | |
|---|---|---|
| EP | 1 391 237 A2 | 2/2004 |
| JP | 2005-199238 A | 7/2005 |
| JP | 2006-121998 A | 5/2006 |
| JP | 2013-510096 A | 3/2013 |
| WO | 2006/018644 A1 | 2/2006 |
| WO | 2007/150030 A2 | 12/2007 |

OTHER PUBLICATIONS

Notification of the First Office Action dated Nov. 3, 2017, issued in corresponding Chinese Application No. 201480068147.2, filed Oct. 16, 2014, 13 pages.
International Search Report and Written Opinion dated Jan. 20, 2015, issued in corresponding International Application No. PCT/US14/60961, filed Oct. 16, 2014, 10 pages.
Notification of Reasons for Refusal dated Aug. 8, 2018, issued in corresponding Japanese Application No. 2016-523932, filed Oct. 16, 2014, 6 pages.

* cited by examiner

**EXAMPLE DEVICE FOR FORMULATING
PARTICLES AT SMALL VOLUME**

**EXAMPLE DEVICE FOR FORMULATING
PARTICLES AT SMALL VOLUME**

DEVICE FOR FORMULATING PARTICLES AT SMALL VOLUMES

FIELD OF THE INVENTION

The present invention relates to manufacturing particles, and devices and methods for formulating the particles at small volumes.

BACKGROUND OF THE INVENTION

Particles are important class of materials in medicine and other applications. Particles exist at nanometer or micrometer sizes and are used in a wide range of applications, including pharmaceuticals, medical devices, research tools, cosmetics, paints and inks, industrial applications, as well as others. For example, a major challenge for many active pharmaceutical ingredients (therapeutic materials) is the inability to deliver adequate concentrations to target cells to elicit a biological affect. Certain therapeutic materials, including many chemotherapeutic materials, are toxic and cannot be administered systemically at doses that are required to have an affect on a disease, while others, including many biologics like oligonucleotide therapeutic materials, are unable to cross cell membranes to access their site of action. Polymers, lipids and other materials offer a promising solution for encapsulating therapeutic materials and transporting them to diseased cells and tissues in particles. Such particles can increase a therapeutic material's therapeutic index by reducing toxicity through shielding the therapeutic material from healthy tissues, increasing the therapeutic material effectiveness through targeting diseased tissue, and by enabling the active delivery of therapeutic materials to their site of action.

A variety of methods have been developed to manufacture particles. These methods include self-assembly, precipitation, and homogenization. Various devices, including microfluidic devices have demonstrated the ability to controllably and rapidly mix fluids in continuous flow formats with precise control over temperature, residence times, and solute concentrations. Microfluidics has proven applications for the synthesis of inorganic nanoparticles and microparticles, and can outperform macroscale systems in large-scale production of particles. Droplet techniques have been applied to produce monodisperse microparticles for therapeutic material delivery or to produce large vesicles for the encapsulation of cells, proteins, or other biomolecules. Hydrodynamic flow focusing, a common microfluidic technique to provide rapid mixing of reagents, has been used to create monodisperse lipid particles of controlled size. This technique has also proven useful in the production of polymer particles where smaller, more monodisperse particles were obtained, with higher encapsulation of small molecules as compared to bulk production methods. Turbulent mixers, including T, W, or Y mixers with channel dimensions >0.1 mm have been successfully used for the manufacture of microparticles and nanoparticles.

Despite the availability of methods of manufacture for particle systems, the manufacture of high quality particles at small scales (<1 mL) remains at challenge due to the difficulties of mixing very small volumes together effectively and the wastage of fluids, or fluidic "dead volume," in the devices and in connections to the devices. The present invention seeks to fulfill this need and provides further related advantages.

SUMMARY OF THE INVENTION

In one aspect of the invention, methods for making particles are provided.

In one embodiment, the method comprises:
(a) introducing a first stream comprising a first solvent into a channel; wherein the channel has a first region adapted for flowing one or more streams introduced into the channel and a second region for mixing the contents of the one or more streams; and wherein the first solvent comprises a therapeutic material and optionally one or more particle-forming materials;
(b) introducing a second stream comprising one or more particle-forming materials and optionally a therapeutic material in a second solvent into the channel to provide first and second streams and wherein the first and second solvents are not the same;
(c) flowing the one or more first streams and the one or more second streams from the first region of the channel into the second region of the channel such that the one or more first streams and the one or more second streams arrive at the second region for mixing at substantially the same time; and
(d) mixing the contents of the one or more first streams and the one or more second streams in the second region of the channel to provide a third stream comprising particles.

In another embodiment, the method comprises:
(a) introducing a stream comprising a first solvent into a channel; wherein the channel has a first region adapted for flowing one or more streams introduced into the channel; and
(b) conducting the first stream through the channel and into a reservoir comprising a second solvent, wherein conducting the first stream into the reservoir comprises mixing the contents of the first stream with the contents of the reservoir to provide particles.

In another aspect, the invention provides devices for making particles.

In one embodiment, the device comprises:
(a) a first well for receiving a first solution comprising a first solvent;
(b) a first channel in fluid communication with the first well;
(c) a second well for receiving a second solution comprising a second solvent;
(d) a second channel in fluid communication with the second well;
(e) a third channel for receiving first and second streams flowed from the first and second wells through the first and second channels, respectively, wherein the third channel has a first region adapted for flowing the first and second streams introduced into the channel and a second region adapted for mixing the contents of the first and second streams to provide a third stream comprising particles; and
(f) a third well for receiving the third stream comprising particles.

In one embodiment, the device comprises:
(a) a first well for receiving a first solution comprising a first solvent;
(b) a first channel in fluid communication with the first well; and
(c) a second well for receiving a second solution comprising a second solvent, wherein the second well further receives a first stream flowed from the first well through the first channel, and wherein the second well is adapted for mixing the contents of the first stream and second solution in the second well to provide a third solution comprising particles.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 10A shows the device plus manifold and FIG. 10B shows the manifold covering the inlet wells of the device. The manifold allows for an empty syringe to be attached and pushing down on the syringe plunger forces the fluids through the mixing device.

DETAILED DESCRIPTION OF THE INVENTION

The present invention provides methods and devices for manufacturing particles at small volumes.

In one aspect, the invention provides methods for making particles that include a therapeutic material.

In another aspect, the invention provides devices for making particles that include a therapeutic material.

In other aspects, the invention provides methods and devices for making lipid nanoparticles, liposome particles, emulsions, or other lipid-containing particles.

In other aspects, the invention provides methods and devices for making lipid nanoparticles, liposome particles, emulsions, or other lipid-containing particles that contain a therapeutic material.

In further aspects, the invention provides methods and devices for making polymer particles.

In other aspects, the invention provides methods and devices for making polymer particles containing a therapeutic material.

In other aspects, the invention provides methods and devices for making particles made by a combination of lipid, polymer, protein, nucleic acid, and other materials.

In another aspect, the invention provides methods and devices for making particles containing polymers, natural polymers, synthetic polymers, synthetic copolymers, semi-synthetic polymers, polymer conjugates, polymer-therapeutic material conjugate, polymer-drug conjugate.

In a further aspect, the invention provides methods and devices for manufacturing particles containing a research reagent at small volumes.

In other aspects, the invention provides methods and devices for making lipid nanoparticles, liposome particles, emulsions, or other lipid-containing particles that contain a research reagent.

In a further aspect of the invention, particles made by the methods and/or devices of the invention are provided.

Methods for Making Particles at Small Volumes

Figure 1:
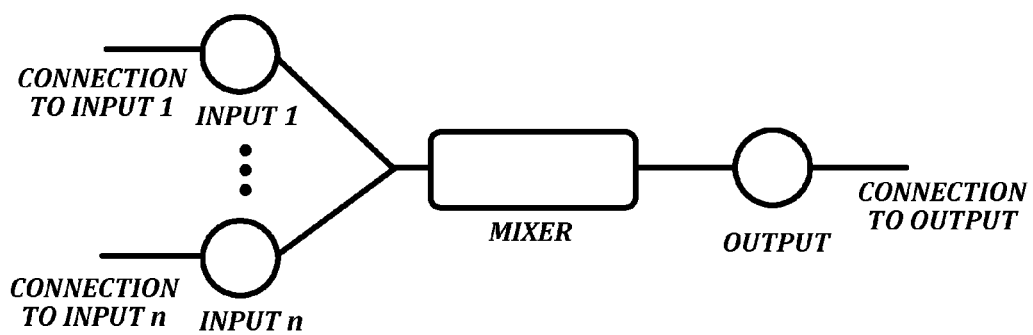
FIG. 1 is a schematic illustration of the challenges of manufacturing particles at small volumes. The illustration includes (a) requirements for timing fluidic mixing to maximize the yield of manufactured particles; (b) areas for fluidic waste.
Figure 2:
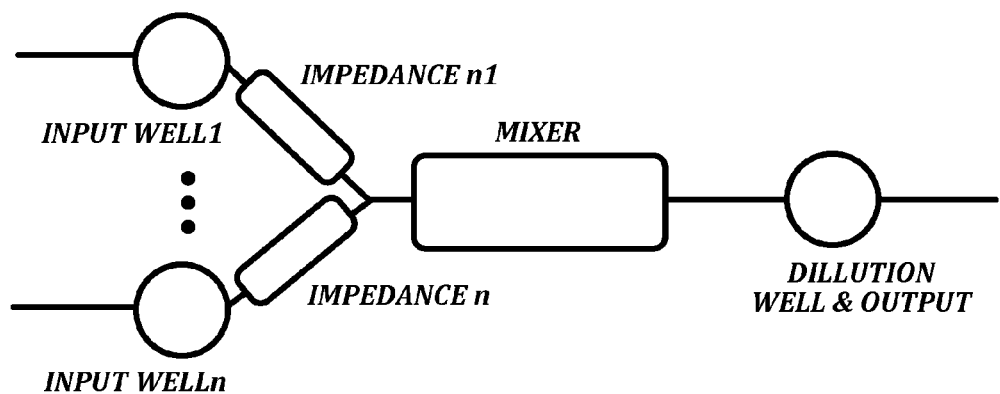
FIG. 2 is a schematic illustration of a representative device and method of the invention for preparing particles at small volumes: a device that uses a combination of input and output reservoirs (wells) to control flow rates and flow timing. In this device, input wells are used to contain input fluids. Channel impedances are used to determine the relative flow rates between flows from the inputs. An outlet well is added. In certain embodiments, a backpressure or stopper is applied to the outlet well to stop fluidic movement from the inputs due to the weight of fluids in the input wells or other phenomena, prior to a pressure applied to the inputs. In certain embodiments, a backpressure is achieved by adding fluid to the outlet well prior to adding fluids to the input wells. In this case fluids with the lowest surface tension are added last because these are the fluids which move through the chip at the highest rate. The input fluids are then added into the input reservoirs and the inputs are pressurized to create fluid flow. Flow rates of the different flows are controlled by the impedances of the channels from the inputs to the mixer chamber. The flows can be timed to reach the mixer at a similar time by pressurizing the input wells simultaneously. In certain embodiments, the device is purged of remaining fluid by applying fluid (gas or liquid) to the inputs and flowed through the mixers following nanoparticle manufacture.
Figure 3:
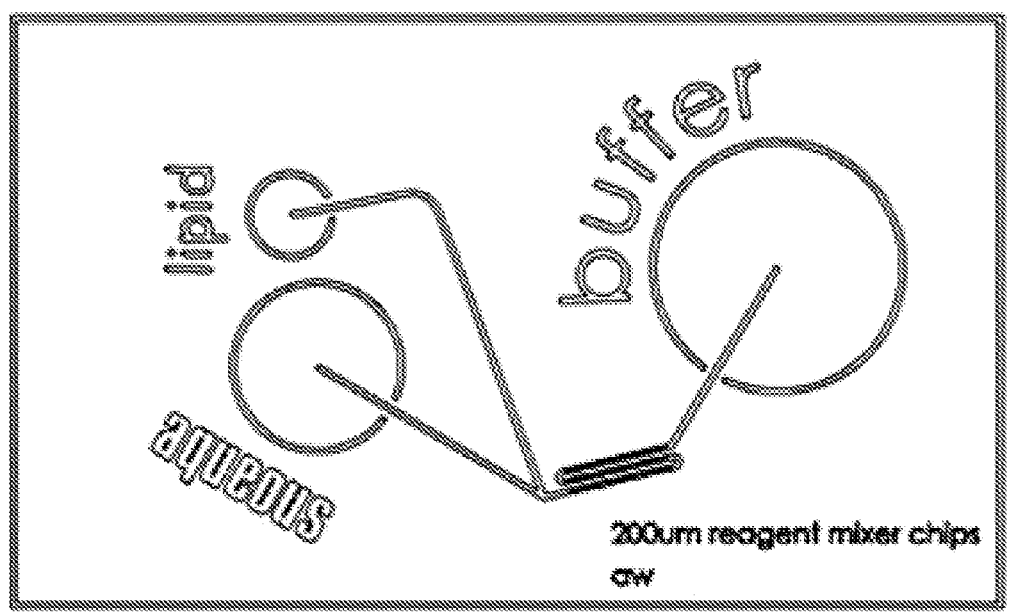
FIG. 3 is an example of a representative device illustrated in the schematic of FIG. 2. This device has two inlet wells (one for an aqueous phase and one for an ethanol/lipid phase) and one outlet well. In practice, a dilution buffer is loaded into the outlet well, this buffer adds backpressure at the output of the device and lowers the ethanol concentration of the final product which stabilizes the particles. Aqueous reagents and lipids in ethanol are loaded into the input wells, a manifold is then clamped oven the inlet wells and pressurized using a syringe or other mechanism. See FIG. 8. The pressurization pushes the reagents in the inlet wells through the mixer (e.g., a staggered herringbone mixer) and into the outlet well. The formulated particles are then recovered using a pipette. The shown device is designed to have a flow ratio of 3 parts aqueous to 1 part ethanol, which is achieved with different channel lengths leading from the input wells to them mixer. In this case, the ratio of 2.5:1 is used and this takes into account the desired flow ratio and the viscosity difference between the input reagents.

In one aspect, the invention provides a method for making particles at small volumes. As used herein, the term "small volume" refers to volumes less than 2 mL and, in certain embodiments, volumes less than 1 mL. The methods of the invention provide particles in volumes in the tens of microliters (e.g., 50, 100, 150, 200, 250, 300, 400, 450, 500, 550, 600, 650, 700, 750, 800, 850, 900, 950 µL). Small volume refers to capability of the devices and methods of the invention to prepare nanoparticles without materials loss. For example, the devices and methods of the invention are capable of manufacturing 100 uL of nanoparticles with no material loss: the volumes of particle-forming materials (e.g., lipids) and therapeutic materials (e.g., RNA) added to the device are about 20 uL each (the remainder of the volume represents the diluting buffer in the additional (e.g., third well of the device) as shown in FIGS. 2 and 3.

In one embodiment, the method for making particles comprises:

(a) introducing a first stream comprising a first solvent into a channel; wherein the channel has a first region adapted for flowing one or more streams introduced into the channel and a second region for mixing the contents of the one or more streams; and wherein the first solvent comprises a therapeutic material and optionally one or more particle-forming materials;

(b) introducing a second stream comprising one or more particle-forming materials and optionally a therapeutic material in a second solvent into the channel to provide first and second streams and wherein the first and second solvents are not the same;

(c) flowing the one or more first streams and the one or more second streams from the first region of the channel into the second region of the channel such that the one or more first streams and the one or more second streams arrive at the second region for mixing at substantially the same time; and (d) mixing the contents of the one or more first streams and the one or more second streams in the second region of the channel to provide a third stream comprising particles.

In the above method, dead volume is minimized and production of particles in small volumes is maximized by combining the first and second streams at substantially the same time prior to mixing. By this method, the mixed volume containing particles comprising the components of each of the first and second streams is minimized.

In one embodiment, one stream (e.g., second stream comprising particle-forming materials in a second solvent such as ethanol) is introduced into the channel in a continuous manner and the flowing stream is interrupted by the introduction of a second stream (e.g., a discrete volume of a first stream comprising therapeutic material) so as to create a plug of a combined volume of the first and second streams. The combined volume is then mixed to provide particles in the combined volume. In this method, the combined volume is preceded and then followed by the second stream. In this method, the relatively valuable first stream comprising the therapeutic material is limiting in the context of therapeutic material-containing particle formation and the second stream comprising the particle-forming materials is used in excess.

In the methods of the invention, the streams to be combined (i.e., first and second stream) are not the same. The composition of each stream can vary and, in certain embodiments, each may include both therapeutic materials and particle-forming materials. It will be appreciated that the composition of each stream is such that particle formation does not occur until the streams are mixed. As further described below, the solvents for the first and second streams are miscible and particles are produced on their mixing. As described herein, the methods and device of the invention are particularly useful for making therapeutic material-containing particles in general, and therapeutic material-containing particles in small volumes in particular.

Figure 6:
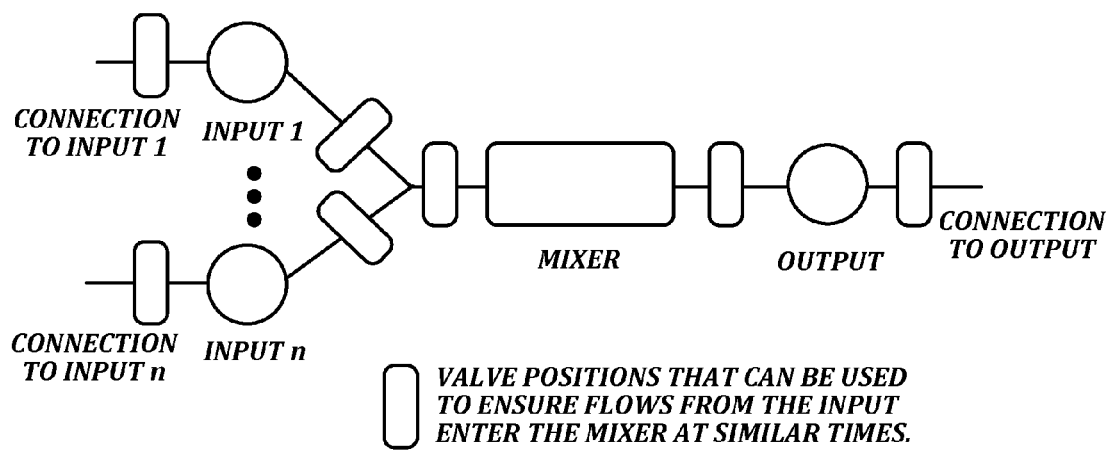
FIG. 6 is a schematic illustration of a representative device and method of the invention for preparing particles at small volumes: a device using valves either at the inlets or outlet to time the introduction of fluidic flows into the mixing chamber.
Figure 7:
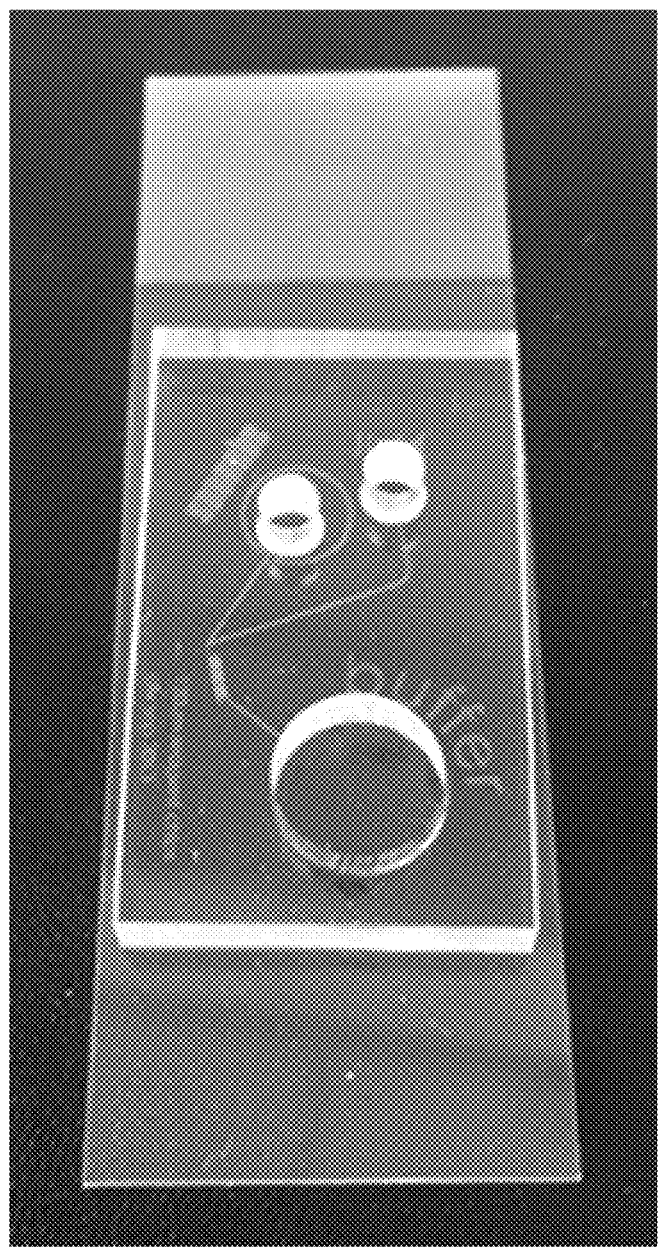
FIG. 7 is an image of a representative device of the invention illustrated schematically in FIGS. 2 and 3.
Figure 8:
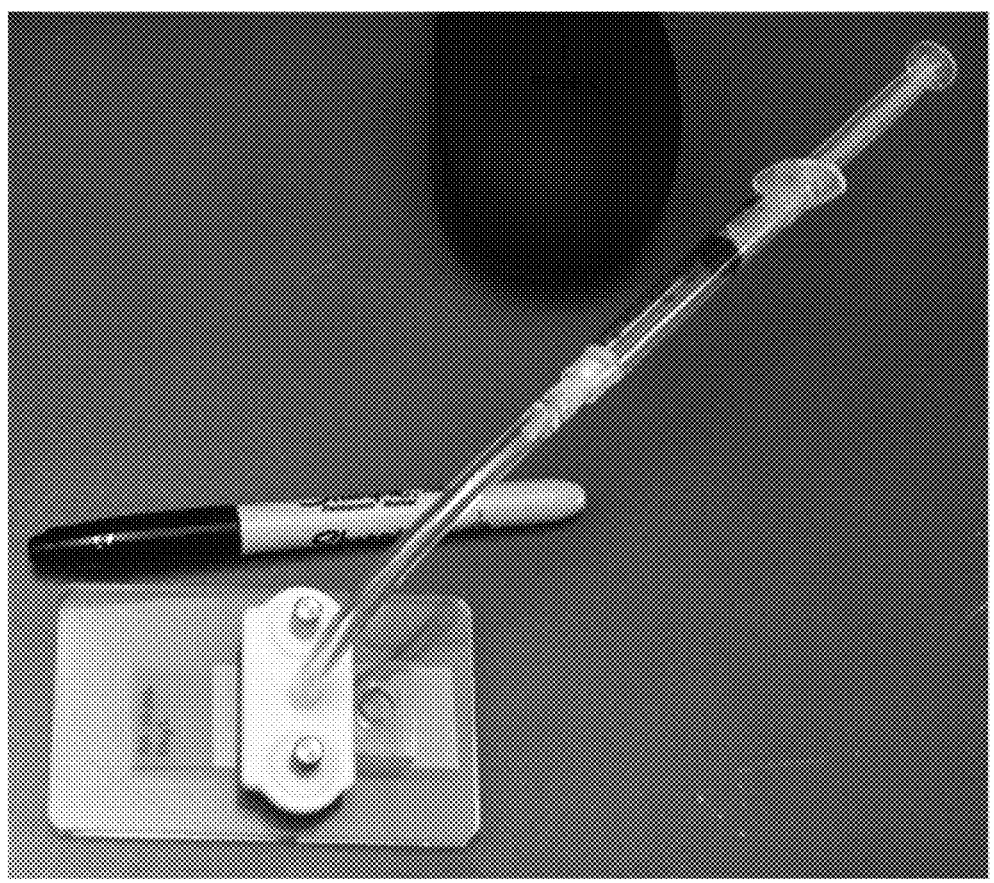
FIG. 8 is an image of the representative device shown in FIG. 7 further including a pressure activated manifold.
Figure 9:
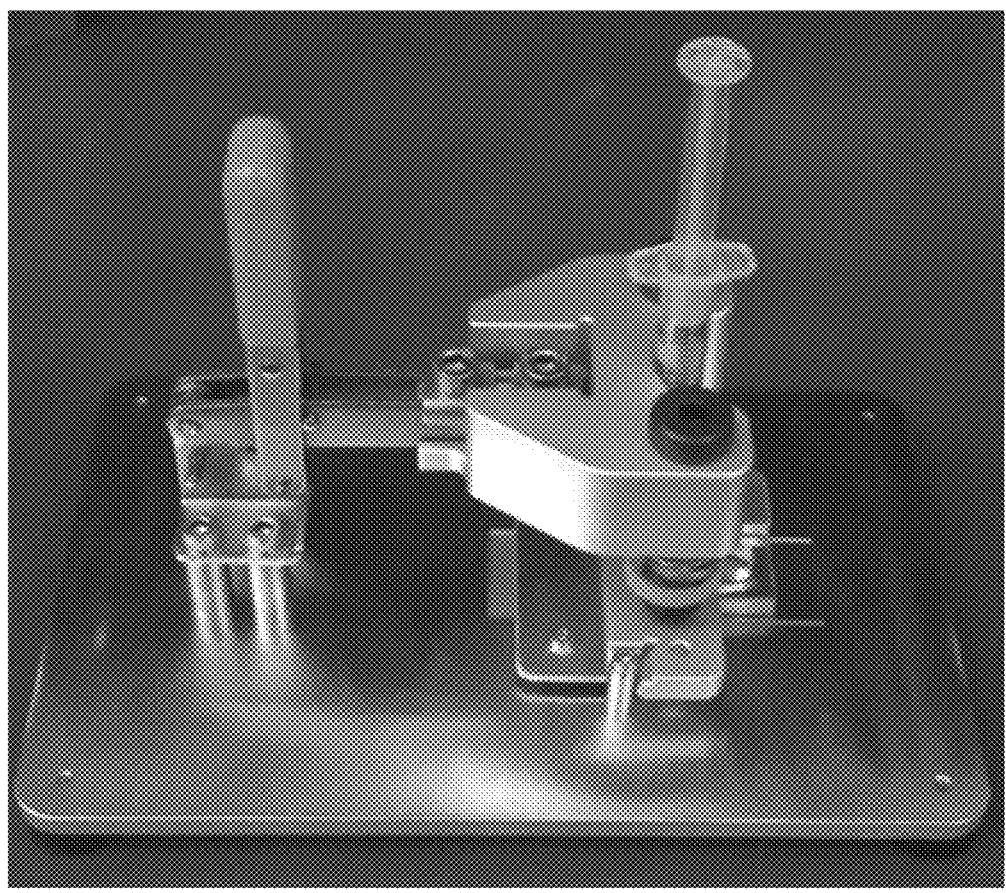
FIG. 9 is an image of the representative device shown in FIG. 7 further including a clamping device and pressure-activated manifold.
Figure 10:
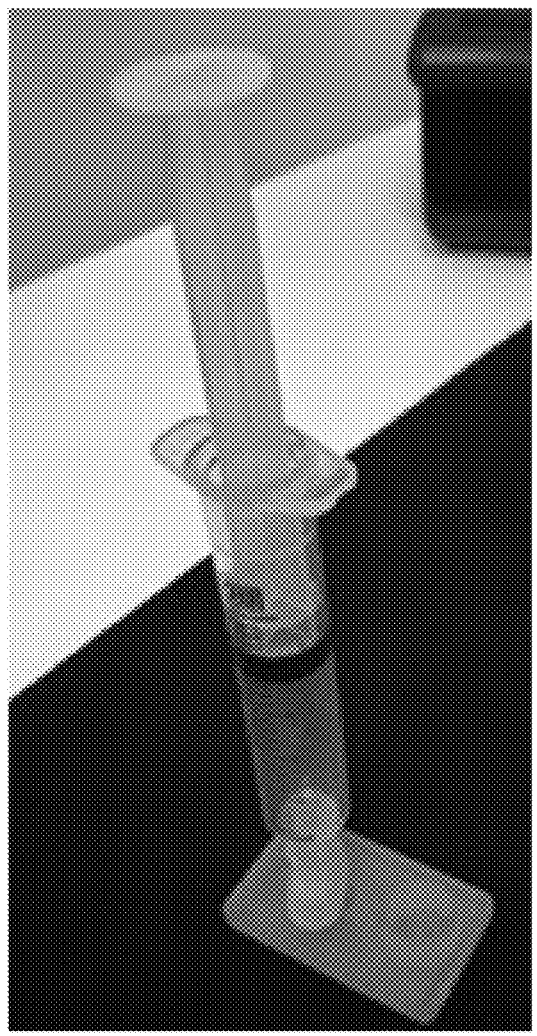
FIG. 10 is an image of a disposable device representative of the device described in FIGS. 2 and 3.
Figure 10:
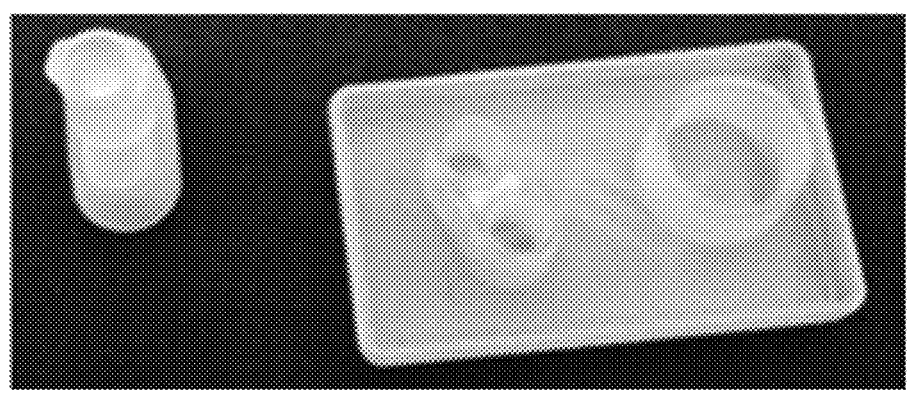

In certain embodiments, the above method further includes one or more of the following features:

(i) flowing the one or more first streams and the one or more second streams from the first region of the channel into the second region of the channel at defined flow ratios established by predetermined pressure drops across one or more of the flow channels, by application of predetermined pressure to one or more of the flow channels, or by a combination of both (see impedances illustrated in FIGS. 2-5);

(ii) flowing a fluid (gas or liquid) into the one or more first streams and/or the one or more second streams after or during making the particles to expel the first and second streams from the from the channels;

(iii) applying a backpressure to the one or more first streams and the one or more second streams sufficient to prevent flow (due to gravity, wicking, or capillary action) into the channels until a predetermined forward pressure is achieved to flow the first stream into the first channel and the second stream into the second channel;

(iv) establishing a backpressure sufficient to prevent flow (due to gravity, wicking, or capillary action) into the first and second channels by physically blocking the output channel until a predetermined forward pressure is achieved to flow the first stream into the first channel and the second stream into the second channel; or (v) using input or output valves in the system to ensure the timing of the flows of the one or more first streams and the one or more second streams from the first region of the channel into the second region (e.g., the first channel further comprising a first input valve effective to time flow of the first stream into the first channel, the second channel further comprising a second input valve effective to time flow of the second stream into the second channel, and/or an output channel further comprising an output valve effective to time flow of the first and/or second streams into the first and second streams, respectively. See, for example, FIG. 6.

In certain embodiments of the methods, the time that either the first stream or the second stream enters the second region of the channel without the other is minimized and the mixing of fluids together is maximized. Timing of the fluid flow may be achieved using valves, pressure, impedance matching, or any other methods to achieve the timing.

In certain embodiments of the above methods, the contents of the first and second streams can be mixed by chaotic advection, turbulent mixing, jetting, vortex methods, and stirring. Mixing may be achieved by an active mixing device or passive mixing device. The mixing may occur in a continuous flow format or in defined volume format. The mixing may be achieved using a microfluidic mixer, including a herringbone mixer, zig-zag mixer, micro-jet mixer, micro-vortex mixer, tesla mixer, tear drop mixer, bubble mixer, acoustic streaming. The mixing may be achieved using a macroscopic mixer, including a T-mixer, Y-mixer, W-mixer, and mixing tubes.

In certain embodiments of the above methods, mixing the contents of the one or more first streams and the one or more second streams comprises varying the concentration or relative mixing rates of the one or more first streams and the one or more second streams. Differing flow rations may be enabled by either differential pressure applied to the flows, differential pressure drops across the flow channels, differential channel impedances, or combination therein, applied to the first and second streams. Differential impedances of the channels through varying the channel heights, widths, lengths, or surface properties, may be used to achieve different flow rates. Fluidic surface tensions, viscosities, and other surface properties of the flows in the one or more first streams and the one or more second streams may be used or considered to achieve different flow rates.

In certain embodiments of the above methods, after or during manufacture of particles, flowing into the one or more first streams and the one or more second streams from the first region of the channel into the second region of the channel a fluid or gas to expel the first stream and second streams. The first and second channel may be fully purged or partially purged under this method. Gases such as air, nitrogen, argon or others may be used. Liquids including water, aqueous buffer, ethanol, oils, or any other liquid may be used.

In certain embodiments of the above methods, backpressures are applied to ensure the flows of the one or more first streams and the one or more second streams from the first region of the channel into the second region is limited until an initial desired input pressure is achieved. This may be achieved by applying pressure to the outlet channels, negative pressures to the input channels. This may be achieved by loading an outlet reservoir with fluid that may or may not be required in the final particle solution.

In certain embodiments of the above methods, the fluids are introduced into the device in ways that minimize fluidic waste. This may be achieved by pipetting fluids into the device, pipetting fluids out of the device, connecting the device to syringes.

In another embodiment, the invention provides a method for making particles comprising:

(a) introducing a stream comprising a first solvent into a channel; wherein the channel has a first region adapted for flowing one or more streams introduced into the channel; and (b) conducting the first stream through the channel and into a reservoir comprising a second solvent, wherein conducting the first stream into the reservoir comprises mixing the contents of the first stream with the contents of the reservoir to provide particles.

Figure 4:
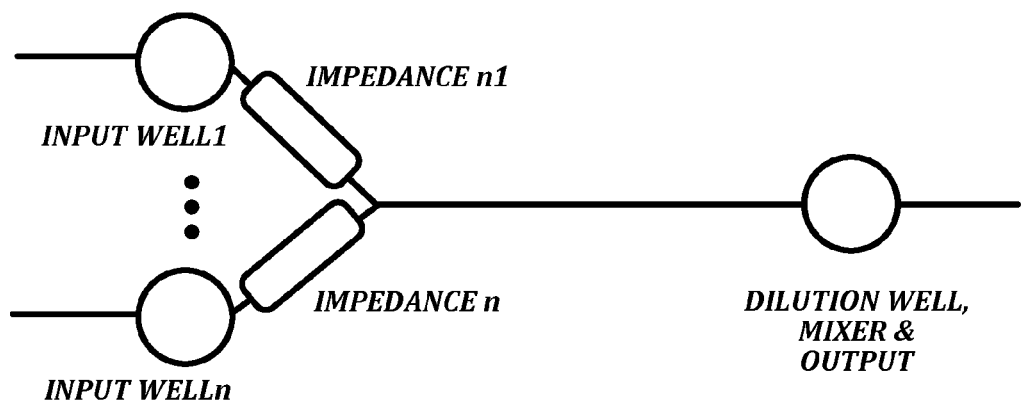
FIG. 4 is a schematic illustration of a representative device and method of the invention for preparing particles at small volumes: a device that flows a first stream of solvent (input wells 1 through n) into a second solvent contained in the outlet reservoir (dilution well). Mixing of the first stream with the contents of the outlet reservoir can occur through various mechanisms including (i) convection flows occurring by introducing the first stream into the reservoir and (ii) active mixing of the combined fluids as the first stream is introduced into the reservoir.
Figure 5:
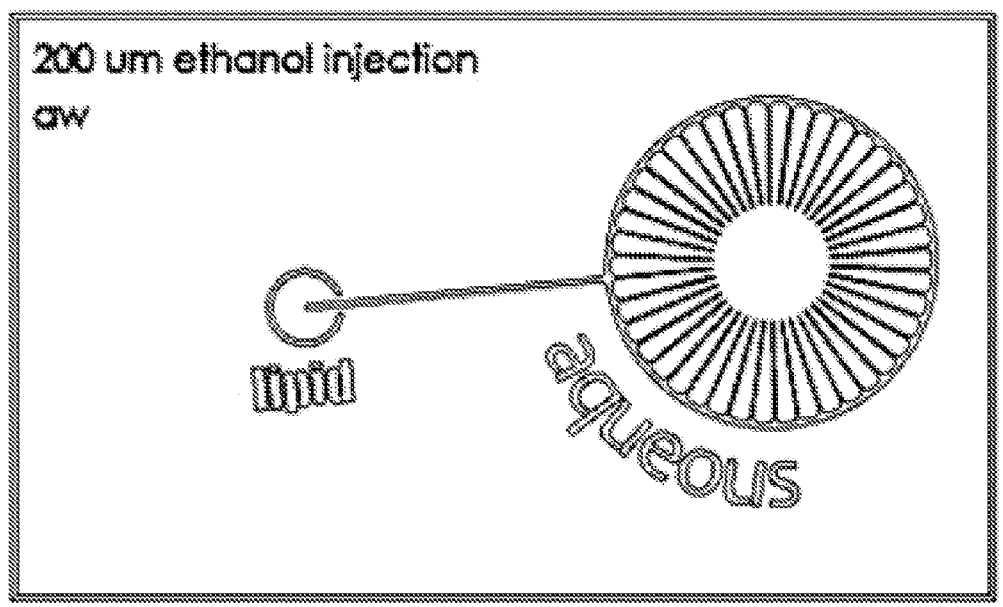
FIG. 5 is an example of a representative device illustrated in the schematic of FIG. 4. The device has a single input well for a lipid/ethanol solution and an outlet well into which an aqueous solution is loaded. The device has a large number of microchannels leading into the outlet well, the impedance of microchannels is high compared to the channel feeding them. This is necessary for an even distribution of fluid. After the reagents are loaded, the inlet well is pressurized. The fluid in the inlet well flows through the microchannels and into the output well. The fluid is mixed by convection and by air bubbles flowing into the outlet well.

This embodiment is illustrated in FIGS. 4 and 5.

In this embodiment, the stream and the reservoir first and second streams are as in the method described above. The first and second solvents are not the same and are miscible. The stream and the reservoir are not the same and each may include a therapeutic material and particle-forming materials. In one embodiment, the stream comprises a first solvent (ethanol) and particle-forming materials and the reservoir comprises a second solvent (aqueous) and a therapeutic material. In another embodiment, the stream comprises a first solvent (aqueous) and a therapeutic material and the reservoir comprises a second solvent (ethanol) and particle-forming materials.

In certain embodiments of this embodiment of the method, the method further includes one or more of features (i)-(v) described above.

Devices for Making Particles at Small Volumes

In another aspect, the invention provides devices for producing particles at small volumes. In certain embodiments, the devices are useful for carrying out the methods of the invention.

In one embodiment, the device includes:

(a) a first well for receiving a first solution comprising a first solvent;

(b) a first channel in fluid communication with the first well;

(c) a second well for receiving a second solution comprising a second solvent;

(d) a second channel in fluid communication with the second well;

(e) a third channel for receiving first and second streams flowed from the first and second wells through the first and second channels, respectively, wherein the third channel has a first region adapted for flowing the first and second streams introduced into the channel and a second region adapted for mixing the contents of the first and second streams to provide a third stream comprising particles; and (f) a third well for receiving the third stream comprising particles.

This embodiment is illustrated in FIGS. 2, 3, and 6-8.

It will be appreciated that devices of the invention can include one or more first wells, one or more first channels, one or more second wells, one or more second channels, one or more third channels, and one or more third wells.

In one embodiment, the device further includes means for diluting the third stream to provide a diluted stream comprising stabilized particles.

In another embodiment, the device includes:

(a) a first well for receiving a first solution comprising a first solvent;

(b) a first channel in fluid communication with the first well; and (c) a second well for receiving a second solution comprising a second solvent, wherein the second well further receives a first stream flowed from the first well through the first channel, and wherein the second well is adapted for mixing the contents of the first stream and second solution in the second well to provide a third solution comprising particles.

This embodiment is illustrated in FIGS. 4 and 5.

It will be appreciated that devices of the invention can include one or more first wells, one or more first channels, and one or more second wells.

In certain embodiments, the devices of the invention are a macrofluidic or microfluidic device. In certain embodiments, the first and second streams can be mixed by chaotic advection, turbulent mixing, jetting, vortex methods, bubble mixing, micro acoustic streaming, stirring, or other mixing methods. Mixing may be achieved by an active mixing device or passive mixing device. The mixing may occur in a continuous flow format or in defined volume format. The mixing may be achieved using a microfluidic mixer, including a herringbone mixer, zig-zag mixer, micro jet mixer, or micro-vortex mixer. The mixing may be achieved using a macroscopic mixer, including a T-mixer, Y-mixer, or W-mixer.

In certain embodiments, the device of the invention is a microfluidic device including one or more microchannels (i.e., a channel having its greatest dimension less than 1 millimeter). In one embodiment, the microchannel has a hydrodynamic diameter from about 20 to about 400 μm. In certain embodiments, the microchannel has two regions: a first region for receiving and flowing at least two streams (e.g., one or more first streams and one or more second streams) into the device. The contents of the first and second streams are mixed in the microchannel's second region. In one embodiment, the second region of the microchannel has a principal flow direction and one or more surfaces having at least one groove or protrusion defined therein, the groove or protrusion having an orientation that forms an angle with the principal direction (e.g., a staggered herringbone mixer), as described in U.S. Patent Application Publication No. 2004/0262223, expressly incorporated herein by reference in its entirety. In one embodiment, the second region of the microchannel comprises bas-relief structures. To achieve maximal mixing rates, it is advantageous to avoid undue fluidic resistance prior to the mixing region. Thus, one embodiment of the invention is a device in which non-microfluidic channels, having dimensions greater than 1000 microns, are used to deliver the fluids to a single mixing channel.

In certain embodiments mixing of the first and second streams can also be accomplished with means for varying the concentration and relative flow rates of the first and second streams. Differing flow rations may be enabled by either differential pressure applied to the flows, differential pressure drops across the flow channels, differential channel impedances, or combination therein, applied to the first and second streams. Differential impedances of the channels through varying the channel heights, widths, lengths, or surface properties, may be used to achieve different flow rates. Fluidic surface tensions, viscosities, and other surface properties of the flows in the one or more first streams and the one or more second streams may be used or considered to achieve different flow rates.

In certain embodiments, the device further includes means for complete or partial purging of the system to minimize the waste volume. After or during manufacture of particles, the device is able to be flown into the one or more first streams and the one or more second streams from the first region of the channel into the second region of the channel a fluid or gas to expel the first stream and second streams. The first and second channel may be fully purged or partially purged under this method. Gasses such as air, nitrogen, argon or others may be used. Liquids including water, aqueous buffer, ethanol, oils, or any other liquid may be used.

In certain embodiments, the device enables backpressures to be applied to ensure the flows of the one or more first streams and the one or more second streams from the first region of the channel into the second region is limited until an initial desired input pressure is achieved. This may be achieved by applying pressure to the outlet channels, negative pressures to the input channels. This may be achieved by loading an outlet reservoir with fluid that may or may not be required in the final particle solution.

In certain embodiments, the device is designed such that fluids are introduced into the device in ways that minimize fluidic waste. This may be achieved by pipetting fluids into the device, pipetting fluids out of the device, connecting the device to syringes, or other methods.

In certain embodiments, the device is microfluidic and produced by soft lithography, the replica molding of microfabricated masters in elastomer. The device has two inlets, one for each of the solutions prepared above, and one outlet. The microfluidic device was produced by soft lithography, the replica molding of microfabricated masters in elastomer. In one example, the device features are 200 µm wide and approximately 70 µm high mixing channel with herringbone structures formed by approximately 25 µm high and 50 µm thick features on the roof of the channel. The device was sealed using an oxygen plasma treatment to a 75×25×1.5 mm glass slide. Other examples, include devices with widths and associated relative dimensions that are smaller (120 µm wide) or larger (300 µm wide). Input and output ports are drilled into the device.

In a second embodiment, the device is microfluidic and produced from a hard thermoplastic such as cyclic olefin copolymer. A negative tool is machined using a CNC mill and devices formed using injection molding. Channel dimensions are preserved with the addition of a draft angle ranging between 1° and 5° on vertical surfaces. Molded pieces are sealed to a blank substrate using a variety of techniques, including but not limited to: lamination, solvent welding, heat pressing and combinations thereof. Bonded devices are annealed to remove residual stresses from the production processes. Once formed, devices are installed and used in the custom instrument in the same way as elastomer devices.

To achieve maximal mixing rates it is advantageous to avoid undue fluidic resistance prior to the mixing region. Thus one embodiment of the invention is a device in which non-microfluidic channels, having dimensions greater than 1000 microns, are used to deliver fluids to a single mixing channel. This device for producing particles includes:

(a) a single inlet channel for receiving a first solution comprising solvent and none or some solution and a second solution comprising particle components in a second solvent; and (b) a second region adapted for mixing the contents of the first and second streams to provide a third stream comprising particles.

In such an embodiment, the first and second streams are introduced into the channel by a single inlet or by one or two channels not having micro-dimensions, for example, a channel or channels having dimensions greater than 1000 µm (e.g., 1500 or 2000 µm or larger). These channels may be introduced to the inlet channel using adjacent or concentric macrosized channels.

In the description above directed to devices of the invention, the compositions of the solvents and streams are as described above for the methods of the invention.

In certain embodiments, the device includes the components described herein and may include additional components. In these embodiments, the device "comprises" the specified components. In other embodiments, the device includes the components described herein and may include additional components that do not alter the characteristics of the devices (e.g., do not include components that alter the inventive aspects of the device). In these embodiments, the device "consists essentially of" the specified components. In further embodiments, the device includes only the components described herein and no others. In these embodiments, the device "consists of" the specified components.

Particles Produced Using the Methods and Devices

In a further aspect of the invention, particles made by the methods and/or devices of the invention are provided.

In certain embodiments of the above methods and devices, the methods and devices are used to manufacture particles that are <100 nm in diameter. In certain embodiments of the above methods and devices, the methods and devices are used to manufacture particles that are >100 nm and <1000 nm in diameter. In certain embodiments of the above methods and devices, the methods and devices are used to manufacture particles that are >1000 nm in diameter.

In the above methods, particles are formed from one or more solutions, streams, or reservoirs that include particle-forming materials. In addition to particle-forming materials, the methods utilize solutions, streams, and reservoirs that include any combination of zero, one or more lipid components; zero, one or more polymer components; zero, one or more protein components; zero, one or more oligonucleotide components; or zero, one or more lipid components.

In certain embodiments, the first solvent (e.g., therapeutic material-containing solution) may include aqueous buffers, for example citrate and acetate buffers, or organic solvents, for example aqueous ethanol, 1,4-dioxane, tetrahydrofuran, acetone, dimethyl sulfoxide, dimethylformamide, acids, and alcohols, and acetonitrile 90%. Molecular components of the particles may or may not be contained in the first stream.

In certain embodiments, the second solvent is miscible with the first solvent. Suitable solvents include aqueous buffers, for example citrate and acetate buffers, or organic solvents, for example, aqueous ethanol, 1,4-dioxane, tetrahydrofuran, acetone, dimethyl sulfoxide, dimethylformamide, acids, and alcohols, and acetonitrile 90%.

In certain embodiments, the particles are formed in a microfluidic process that utilizes relatively rapid mixing and high flow rates. The rapid mixing provides particles having the advantageous properties including size, homogeneity, encapsulation efficiency. Mixing rates used in the practice of the methods of the invention range from about 100 μsec to about 20 msec. Representative mixing rates include from about 0.5 to about 20 msec.

In one application of the present invention the methods and devices are used for making lipid particles containing a bioactive agent. In the methods and devices, a first stream comprising an polynucleic acid in a first solvent and a second stream comprising lipid particle-forming materials in a second solvent are introduced into a channel having a first region adapted for receiving and flowing the streams introduced therein and a second region for mixing the contents of the two streams to provide a third stream comprising lipid particles with encapsulated therapeutic agent.

In one aspect, the invention provides a method for making lipid particles containing a therapeutic agent. In one embodiment, the method includes (a) introducing a first stream comprising a polynucleic acid in a first solvent into a channel; wherein the channel has a first region adapted for flowing one or more streams introduced into the channel and a second region for mixing the contents of the one or more streams;

(b) introducing a second stream comprising lipid particle-forming materials in a second solvent in the channel to provide first and second streams flowing, wherein the lipid particle-forming materials comprise an ionizable lipid, and wherein the first and second solvents are not the same;

(c) flowing the one or more first streams and the one or more second streams from the first region of the channel into the second region of the channel; and (d) mixing of the contents of the one or more first streams and the one or more second streams flowing in the second region of the channel to provide a third stream comprising lipid particles with encapsulated polynucleic acids.

In certain embodiments of this embodiment, the method further includes one or more of features (i)-(v) described above.

The contents of the first and second streams can be mixed by chaotic advection. In one embodiment, mixing the contents of the one or more first streams and the one or more second streams comprises varying the concentration or relative mixing rates of the one or more first streams and the one or more second streams.

To stabilize the third stream containing the lipid particles with encapsulated polynucleic acids, the method can further include comprising diluting the third stream with an aqueous buffer. In one embodiment, diluting the third stream includes flowing the third stream and an aqueous buffer into a second mixing structure. In another embodiment, the aqueous buffer comprising lipid particles with encapsulated polynucleic acids is dialyzed to reduce the amount of the second solvent.

The first stream includes a polynucleic acid in a first solvent. Suitable first solvents include solvents in which the polynucleic acids are soluble and that are miscible with the second solvent. Suitable first solvents include aqueous buffers. Representative first solvents include citrate and acetate buffers.

The second stream includes lipid particle-forming materials in a second solvent. Suitable second solvents include solvents in which the ionizable lipids are soluble and that are miscible with the first solvent. Suitable second solvents include aqueous alcohols. Representative second solvents include aqueous ethanol 90%.

The methods of the invention have a polynucleic acid encapsulation efficiency is from about 60% to about 100%. In certain embodiments, the polynucleic acid encapsulation efficiency is about 100%.

In a further aspect, the invention provides lipid particles made by the methods and/or devices of the invention. The lipid particles of the invention have a diameter from about 30 to about 200 nm. In one embodiment, the lipid particles have a diameter of about 80 nm.

Advantageously, the lipid particles include from about 1 to about 5 mole percent PEG-lipid, PEG-based surfactant, or other stabilizing agent. In one embodiment, the lipid particles include about 1.5 mole percent PEG-lipid. In one embodiment, the lipid particles include about 1-10 mole percent surfactants. In one embodiment, the lipid particles include about 2.5 mole percent stabilizing agent, like a surfactant.

Definitions

Lipid Nanoparticles

In one aspect, the invention provides lipid nanoparticles containing anionic macromolecule(s). The lipid nanoparticles include one or more cationic lipids, one or more second lipids, and one or more nucleic acids.

Cationic Lipids

The lipid nanoparticles include a cationic lipid. As used herein, the term "cationic lipid" refers to a lipid that is cationic or becomes cationic (protonated) as the pH is lowered below the pK of the ionizable group of the lipid, but is progressively more neutral at higher pH values. At pH values below the pK, the lipid is then able to associate with negatively charged nucleic acids (e.g., oligonucleotides). As used herein, the term "cationic lipid" includes zwitterionic lipids that assume a positive charge on pH decrease.

The term "cationic lipid" refers to any of a number of lipid species which carry a net positive charge at a selective pH, such as physiological pH. Such lipids include, but are not limited to, N,N-dioleyl-N,N-dimethylammonium chloride (DODAC); N-(2,3-dioleyloxy)propyl)-N,N,N-trimethylammonium chloride (DOTMA); N,N-distearyl-N,N-dimethylammonium bromide (DDAB); N-(2,3-dioleoyloxy)propyl)-N,N,N-trimethylammonium chloride (DOTAP); 3-(N—(N', N'-dimethylaminoethane)-carbamoyl)cholesterol (DC-Chol); and N-(1,2-dimyristyloxyprop-3-yl)-N,N-dimethyl-N-hydroxyethyl ammonium bromide (DMRIE). Additionally, a number of commercial preparations of cationic lipids are available which can be used in the present invention. These include, for example, LIPOFECTIN® (commercially available cationic liposomes comprising DOTMA and 1,2-dioleoyl-sn-3-phosphoethanolamine (DOPE), from GIBCO/BRL, Grand Island, N.Y.); LIPO-FECTAMINE® (commercially available cationic liposomes comprising N-(1-(2,3-dioleyloxy)propyl)-N-(2-(spermin-ecarboxamido)ethyl)-N,N-dimethyl-ammonium trifluoroacetate (DOSPA) and (DOPE), from GIBCO/BRL); and TRANSFECTAM® (commercially available cationic lipids comprising dioctadecylamidoglycylcarboxyspermine (DOGS) in ethanol from Promega Corp., Madison, Wis.). The following lipids are cationic and have a positive charge at below physiological pH: DODAP, DODMA, DMDMA, 1,2-dilinoleyloxy-N,N-dimethylaminopropane (DLinDMA), 1,2-dilinolenyloxy-N,N-dimethylaminopropane (DLenDMA), 1,17-bis(2-octylcyclopropyl)heptadecan-9-yl 4-(dimethylamino) butanoate.

In one embodiment, the cationic lipid is an amino lipid. Suitable amino lipids useful in the invention include those described in WO 2012/016184, incorporated herein by reference in its entirety. Representative amino lipids include 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethyl-aminopropane chloride salt (DLin-TAP.Cl), 1,2-dilinoley-loxy-3-(N-methylpiperazino)propane (DLin-MPZ), 3-(N,N-dilinoleylamino)-1,2-propanediol (DLinAP), 3-(N,N-dioleylamino)-1,2-propanediou (DOAP), 1,2-dilinoleyloxo-3-(2-N,N-dimethylamino)ethoxypropane (DLin-EG-DMA), and 2,2-dilinoleyl-4-dimethylaminomethyl-[1,3]-dioxolane (DLin-K-DMA).

Suitable amino lipids include those having the formula:

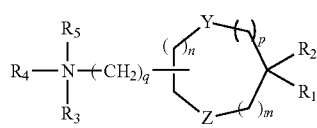

wherein $R_1$ and $R_2$ are either the same or different and independently optionally substituted C10-C24 alkyl, optionally substituted C10-C24 alkenyl, optionally substituted C10-C24 alkynyl, or optionally substituted C10-C24 acyl;

$R_3$ and $R_4$ are either the same or different and independently optionally substituted C1-C6 alkyl, optionally substituted C2-C6 alkenyl, or optionally substituted C2-C6 alkynyl or $R_3$ and $R_4$ may join to form an optionally substituted heterocyclic ring of 4 to 6 carbon atoms and 1 or 2 heteroatoms chosen from nitrogen and oxygen;

$R_5$ is either absent or present and when present is hydrogen or C1-C6 alkyl;

m, n, and p are either the same or different and independently either 0 or 1 with the proviso that m, n, and p are not simultaneously 0;

q is 0, 1, 2, 3, or 4; and

Y and Z are either the same or different and independently O, S, or NH.

In another embodiment, the cationic lipid has the formula:

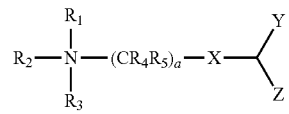

or a pharmaceutically acceptable salt thereof, wherein:

$R_1$ and $R_2$ are each independently H, alkyl, alkenyl, alkynyl, cycloalkyl, aryl, heteroaryl, and heterocyclyl, wherein each of alkyl, alkenyl, alkynyl, cycloalkyl, aryl, heteroaryl, and heterocyclyl is optionally substituted by H; halo; hydroxy; cyano; oxo; $C_1$-$C_6$ alkyl optionally substituted by halo, hydroxy, or alkoxy;

or $R_1$ and $R_2$ are taken together with the N atom to which they are both attached to form a 3-8 member heteroaryl or heterocyclyl; wherein each of the heteroaryl and heterocyclyl is optionally substituted by H; halo; hydroxy; cyano; oxo; nitro; $C_1$-$C_6$ alkyl optionally substituted by halo, hydroxyl, or alkoxy;

$R_3$ is absent, H, alkyl, alkenyl, alkynyl, cycloalkyl, aryl, heteroaryl, or heterocyclyl;

$R_4$ and $R_5$ are each independently H, alkyl, alkenyl, alkynyl, cycloalkyl, aryl, heteroaryl, or heterocyclyl;

wherein each of alkyl, alkenyl, alkynyl, cycloalkyl, aryl, heteroaryl, and heterocyclyl is optionally substituted by H; halo; hydroxy; cyano; oxo; $C_1$-$C_6$ alkyl optionally substituted by halo, hydroxy, or alkoxy;

X is —O—, —S—, —NR$_4$—, —S—S—, —OC(=O)—, —C(=O)O—, —OC(=O)O—, —NR$_4$C(=O)—, C(=O)NR$_4$—, —NR$_4$C(=O)O—, —OC(=O)NR$_4$—, —NR$_4$C(=O)NR$_4$—, —NR$_4$C(=S)O—, OC(=S)NR$_4$—, —NR$_4$C(=S)NR$_4$—, —CR$_4$R$_5$—;

Y and Z are independently $C_{10}$ to $C_{30}$ groups having the formula $L_1$-(CR$_6$R$_7$)$_\alpha$-[L$_2$-(CR$_6$R$_7$)$_\beta$]$_\gamma$-L$_3$-R$_8$, wherein $L_1$ is a bond, —(CR$_6$R$_7$)—, —O—, —CO—, —NR$_8$—, —S—, or a combination thereof;

each $R_6$ and $R_7$, independently, is H; halo; hydroxyl; cyano; $C_1$-$C_6$ alkyl optionally substituted by halo, hydroxyl, or alkoxy:

$L_2$ is a bond, —(CR$_6$R$_7$)—, —O—, —CO—, —NR$_8$—, —S—,

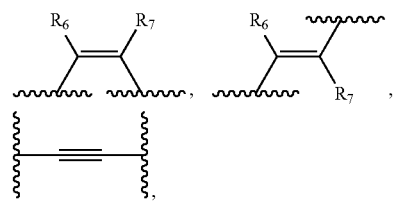

or a combination thereof, or has the formula

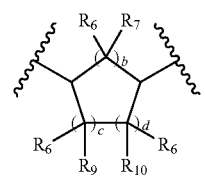

wherein b, c, and d are each independently 0, 1, 2, or 3, given the sum of b, c, and d is at least 1 and no greater than 8; and $R_9$ and $R_{10}$ are each independently $R_7$, or adjacent $R_9$ and $R_{10}$, taken together, are optionally a bond;

$L_3$ is a bond, —$(CR_6R_7)$—, —O—, —CO—, —$NR_8$—, —S—,

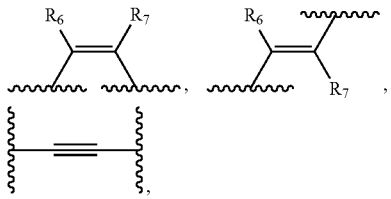

or a combination thereof $R_8$ is independently H; halo; hydroxy; cyano; C1-C6 alkyl optionally substituted by halo, hydroxy, or alkoxy; aryl; heteroaryl; or heterocyclyl; or $R_8$ has the formula:

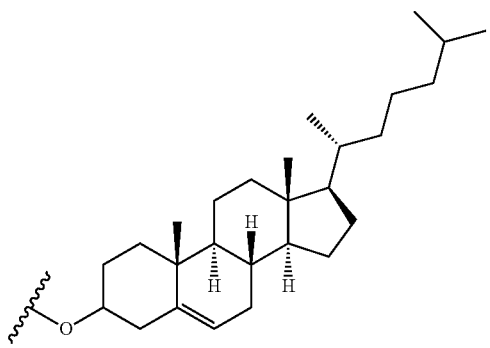

a is 0, 1, 2, 3, or 4;
α is 0-6;
each β, independently, is 0-6;
γ is 0-6.

Other suitable cationic lipids include cationic lipids, which carry a net positive charge at about physiological pH, in addition to those specifically described above, N,N-dioleyl-N,N-dimethylammonium chloride (DODAC); N-(2, 3-dioleyloxy)propyl-N,N—N-triethylammonium chloride (DOTMA); N,N-distearyl-N,N-dimethylammonium bromide (DDAB); N-(2,3-dioleoyloxy)propyl)-N,N,N-trimethylammonium chloride (DOTAP); 1,2-dioleyloxy-3-trimethylaminopropane chloride salt (DOTAP.Cl); 3.beta.-(N—(N', N'-dimethylaminoethane)carbamoyl)cholesterol (DC-Chol), N-(1-(2,3-dioleoyloxy)propyl)-N-2-(sperminecarboxamido) ethyl)-N,N-dimethylammoniumtrifluoracetate (DOSPA), dioctadecylamidoglycylcarboxyspermine (DOGS), 1,2-dioleoyl-3-dimethylammonium propane (DODAP), N,N-dimethyl-2,3-dioleoyloxy)propylamine (DODMA), and N-(1,2-dimyristyloxyprop-3-yl)-N,N-dimethyl-N-hydroxyethyl ammonium bromide (DMRIE). Additionally, a number of commercial preparations of cationic lipids can be used, such as, e.g., LIPOFECTIN® (including DOTMA and DOPE, available from GIBCO/BRL), and LIPOFECTAMINE® (comprising DOSPA and DOPE, available from GIBCO/BRL).

The cationic lipid is present in the particle in an amount from about 30 to about 95 mole percent. In one embodiment, the cationic lipid is present in an amount from about 30 to about 70 mole percent. In one embodiment, the cationic lipid is present in an amount from about 40 to about 60 mole percent.

Neutral Lipids

In certain embodiments, the particle includes one or more neutral lipids.

The term "lipid" refers to a group of organic compounds that are esters of fatty acids and are characterized by being insoluble in water but soluble in many organic solvents. Lipids are usually divided in at least three classes: (1) "simple lipids" which include fats and oils as well as waxes; (2) "compound lipids" which include phospholipids and glycolipids; and (3) "derived lipids" such as steroids.

The term "neutral lipid" refers to any one of a number of lipid species that exist in either an uncharged or neutral zwitterionic form at physiological pH. Representative neutral lipids include diacylphosphatidylcholines, diacylphosphatidylethanolamines, ceramides, sphingomyelins, dihydrosphingomyelins, cephalins, and cerebrosides.

Exemplary lipids include, for example, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoylphosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearioyl-2-oleoyl-phosphatidyethanol amine (SOPE), and 1,2-dielaidoyl-sn-glycero-3-phophoethanolamine (transDOPE).

In one embodiment, the neutral lipid is 1,2-distearoyl-sn-glycero-3-phosphocholine (DSPC).

Sterols

In certain embodiments, the particle includes one or more sterols.

The term "sterol" refers to a subgroup of steroids also known as steroid alcohols. Sterols are usually divided into two classes: (1) plant sterols also known as "phytosterols" and (2) animal sterols also known as "zoosterols."

Exemplary sterols include, for example, campesterol, sitosterol, stigmasterol, ergosterol, and cholesterol. In one embodiment, the sterol is cholesterol.

Surfactants

In certain embodiments, the particle includes one or more surfactants.

The term surfactant as used herein, refers to non-ionic, amphipathic compounds that contain both hydrophobic groups and hydrophilic groups.

In one embodiment, a surfactant is represented by the formula

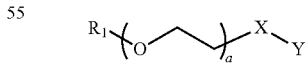

wherein
$R_1$ is H, $C_1$-$C_6$ alkyl;
X is —O—, —S—, —$NR_2$—, —S—S—, —OC(=O)—, —C(=O)O—, —OC(=O)O—, —$NR_2$C(=O)—, C(=O) $NR_2$—, —$NR_2$C(=O)O—, —OC(=O)$NR_2$—, —$NR_2$C(=O)$NR_2$—, —$NR_2$C(=S)O—, OC(=S)$NR_2$—, —$NR_2$C(=S)$NR_2$—, —$CR_2R_3$—;
$R_2$ and $R_3$ are each independently H, alkyl, alkenyl, alkynyl, cycloalkyl, aryl, heteroaryl, or heterocyclyl;

wherein each of alkyl, alkenyl, alkynyl, cycloalkyl, aryl, heteroaryl, and heterocyclyl is optionally substituted by H; halo; hydroxy; cyano; oxo; $C_1$-$C_6$ alkyl optionally substituted by halo, hydroxy, or alkoxy;

Y is a $C_{10}$ to $C_{40}$ group having the formula $L_1$-$(CR_4R_5)_\alpha$-$[L_2$-$(CR_4R_5)_\beta]_\gamma$-$L_3$-$R_6$, wherein:

$L_1$ is a bond, —$(CR_4R_5)$—, —O—, —CO—, —$NR_2$—, —S—, or a combination thereof; each $R_4$ and $R_5$, independently, is H; halo; hydroxyl; cyano; $C_1$-$C_6$ alkyl optionally substituted by halo, hydroxyl, or alkoxy;

$L_2$ and $L_3$ each, independently, are a bond, —$(CR_4R_5)$—, —O—, —CO—, —$NR_2$—, —S—,

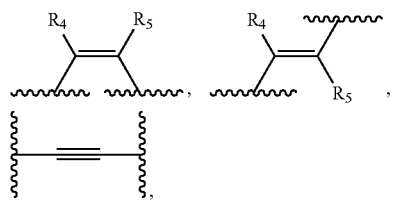

or a combination thereof;

$R_6$ is independently H; halo; hydroxy; cyano; $C_1$-$C_6$ alkyl optionally substituted by halo, hydroxy, or alkoxy; aryl; heteroaryl; or heterocyclyl; or $R_6$ has the formula:

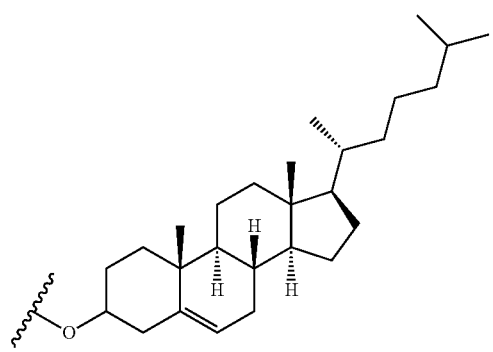

a is 2-100;

α is 0-6;

each β, independently, is 0-6;

γ is 0-6.

In another embodiment, a surfactant is represented by the formula

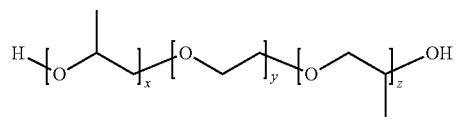

wherein:

x=1 to 50;

y=1 to 50; and z=1 to 50.

In another embodiment, a surfactant is represented by the formula

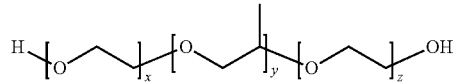

wherein:

x=1 to 50;

y=1 to 50; and z=1 to 50.

In certain embodiments, the surfactant is selected from the group consisting of polyoxyethylene alkyl ethers, polyoxyethylene alkyl esters, diblock co-polymers and triblock co-polymers. Suitable surfactants include polyoxyethylene (20) oleyl ether, polyoxyethylene (23) lauryl ether, polyoxyethylene (40) stearate, poly(propylene glycol)$_{11}$-block-poly(ethylene glycol)$_{16}$-block-poly(propylene glycol)$_{11}$, poly(propylene glycol)$_{12}$-block-poly(ethylene glycol)$_{28}$-block-poly(propylene glycol)$_{12}$.

In certain embodiments, the surfactant is present in the particle in an amount from about 0.1 to about 20 mole percent. In one embodiment, the surfactant is present in an amount from about 0.5 to about 10 mole percent. In one embodiment, the surfactant is present in the lipid nanoparticle in about 2 mole percent.

In one embodiment, the surfactant is polyoxyethylene (20) oleyl ether.

In one embodiment, the surfactant is polyoxyethylene (40) stearate.

Anionic Macromolecules

The lipid nanoparticles of the present invention are useful for the systemic or local delivery of anionic macromolecules.

As used herein, the term "anionic macromolecule" refers to a macromolecule that is anionic or becomes anionic (deprotonated) as the pH is increased above the pK of the ionizable group of the macromolecule, but is progressively more neutral at lower pH values. At pH values above the pK, the macromolecule is then able to associate with positively charged lipids (e.g., cationic lipids). As used herein, the term "anionic macromolecule" includes zwitterionic macromolecules that assume a negative charge on pH increase.

The term "anionic macromolecule" refers to any of a number of species which carry a net negative charge at a selective pH, such as physiological pH. Such macromolecules include, but are not limited to, nucleic acids, proteins, peptides and carbohydrates.

Nucleic Acids

The lipid nanoparticles of the present invention are useful for the systemic or local delivery of nucleic acids.

As used herein, the term "nucleic acid" is meant to include any oligonucleotide or polynucleotide. Fragments containing up to 50 nucleotides are generally termed oligonucleotides, and longer fragments are called polynucleotides. In particular embodiments, oligonucleotides of the present invention are 20-50 nucleotides in length. In the context of this invention, the terms "polynucleotide" and "oligonucleotide" refer to a polymer or oligomer of nucleotide or nucleoside monomers consisting of naturally occurring bases, sugars and intersugar (backbone) linkages. The terms "polynucleotide" and "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases. Oligonucleotides are classified as deoxyribooligonucleotides or ribooligonucleotides. A deoxyribooligonucleotide consists of a 5-carbon sugar called deoxyribose joined covalently to phosphate at the 5' and 3' carbons of this sugar to form an alternating, unbranched polymer. A ribooligonucleotide consists of a similar repeating structure where the 5-carbon sugar is ribose. The nucleic acid that is present in a lipid nanoparticle according to this invention includes any form of nucleic acid that is known. The nucleic acids used herein can be single-stranded DNA or RNA, or double-stranded DNA or RNA, or DNA-RNA hybrids. Examples of double-stranded DNA include structural genes, genes including control and termination regions, and self-replicating systems such as viral or plasmid DNA. Examples of double-stranded RNA include siRNA and other RNA interference reagents. Single-stranded nucleic acids include antisense oligonucleotides, ribozymes, microRNA, mRNA and triplex-forming oligonucleotides.

In one embodiment, the polynucleic acid is an antisense oligonucleotide. In certain embodiments, the nucleic acid is an antisense nucleic acid, a ribozyme, tRNA, snRNA, siRNA, shRNA, ncRNA, miRNA, mRNA, pre-condensed DNA, or an aptamer.

The term "nucleic acids" also refers to ribonucleotides, deoxynucleotides, modified ribonucleotides, modified deoxyribonucleotides, modified phosphate-sugar-backbone oligonucleotides, other nucleotides, nucleotide analogs, and combinations thereof, and can be single stranded, double stranded, or contain portions of both double stranded and single stranded sequence, as appropriate.

The term "nucleotide," as used herein, generically encompasses the following terms, which are defined below: nucleotide base, nucleoside, nucleotide analog, and universal nucleotide.

The term "nucleotide base," as used herein, refers to a substituted or unsubstituted parent aromatic ring or rings. In some embodiments, the aromatic ring or rings contain at least one nitrogen atom. In some embodiments, the nucleotide base is capable of forming Watson-Crick and/or Hoogsteen hydrogen bonds with an appropriately complementary nucleotide base. Exemplary nucleotide bases and analogs thereof include, but are not limited to, purines such as 2-aminopurine, 2,6-diaminopurine, adenine (A), ethenoadenine, N6-2-isopentenyladenine (6iA), N6-2-isopentenyl-2-methylthioadenine (2 ms6iA), N6-methyladenine, guanine (G), isoguanine, N2-dimethylguanine (dmG), 7-methylguanine (7mG), 2-thiopyrimidine, 6-thioguanine (6sG) hypoxanthine and 06-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, 04-methylthymine, uracil (U), 4-thiouracil (4sU) and 5,6-dihydrouracil (dihydrouracil; D); indoles such as nitroindole and 4-methylindole; pyrroles such as nitropyrrole; nebularine; base (Y). In some embodiments, nucleotide bases are universal nucleotide bases. Additional exemplary nucleotide bases can be found in Fasman, 1989, Practical Handbook of Biochemistry and Molecular Biology, pp. 385-394, CRC Press, Boca Raton, Fla., and the references cited therein. Further examples of universal bases can be found, for example, in Loakes, N. A. R. 2001, 29:2437-2447 and Seela N. A. R. 2000, 28:3224-3232.

The term "nucleoside," as used herein, refers to a compound having a nucleotide base covalently linked to the C-1' carbon of a pentose sugar. In some embodiments, the linkage is via a heteroaromatic ring nitrogen. Typical pentose sugars include, but are not limited to, those pentoses in which one or more of the carbon atoms are each independently substituted with one or more of the same or different —R, —OR, —NRR or halogen groups, where each R is independently hydrogen, (C1-C6) alkyl or (C5-C14) aryl. The pentose sugar may be saturated or unsaturated. Exemplary pentose sugars and analogs thereof include, but are not limited to, ribose, 2'-deoxyribose, 2'-(C1-C6)alkoxyribose, 2'-(C5-C14)aryloxyribose, 2',3'-dideoxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose. Also see, e.g., 2'-O-methyl, 4'-.alpha.-anomeric nucleotides, 1'-alpha-anomeric nucleotides (Asseline (1991) Nucl. Acids Res. 19:4067-74), 2'-4'- and 3'-4'-linked and other "locked" or "LNA," bicyclic sugar modifications (WO 98/22489; WO 98/39352; WO 99/14226). "LNA" or "locked nucleic acid" is a DNA analogue that is conformationally locked such that the ribose ring is constrained by a methylene linkage between the 2'-oxygen and the 3'- or 4'-carbon. The conformation restriction imposed by the linkage often increases binding affinity for complementary sequences and increases the thermal stability of such duplexes.

Sugars include modifications at the 2'- or 3'-position such as methoxy, ethoxy, allyloxy, isopropoxy, butoxy, isobutoxy, methoxyethyl, alkoxy, phenoxy, azido, amino, alkylamino, fluoro, chloro and bromo. Nucleosides and nucleotides include the natural D configurational isomer (D-form), as well as the L configurational isomer (L-form) (Beigelman, U.S. Pat. No. 6,251,666; Chu, U.S. Pat. No. 5,753,789; Shudo, EP0540742; Garbesi (1993) Nucl. Acids Res. 21:4159-65; Fujimori (1990) J. Amer. Chem. Soc. 112:7435; Urata, (1993) Nucleic Acids Symposium Ser. No. 29:69-70). When the nucleobase is purine, e.g., A or G, the ribose sugar is attached to the N9-position of the nucleobase. When the nucleobase is pyrimidine, e.g., C, T or U, the pentose sugar is attached to the N1-position of the nucleobase (Kornberg and Baker, (1992) DNA Replication, 2nd Ed., Freeman, San Francisco, Calif.).

One or more of the pentose carbons of a nucleoside may be substituted with a phosphate ester. In some embodiments, the phosphate ester is attached to the 3'- or 5'-carbon of the pentose. In some embodiments, the nucleosides are those in which the nucleotide base is a purine, a 7-deazapurine, a pyrimidine, a universal nucleotide base, a specific nucleotide base, or an analog thereof.

The term "nucleotide analog," as used herein, refers to embodiments in which the pentose sugar and/or the nucleotide base and/or one or more of the phosphate esters of a nucleoside may be replaced with its respective analog. In some embodiments, exemplary pentose sugar analogs are those described above. In some embodiments, the nucleotide analogs have a nucleotide base analog as described above. In some embodiments, exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, and may include associated counterions. Other nucleic acid analogs and bases include for example intercalating nucleic acids (INAs, as described in Christensen and Pedersen, 2002), and AEGIS bases (Eragen, U.S. Pat. No. 5,432,272). Additional descriptions of various nucleic acid analogs can also be found for example in (Beaucage et al., Tetrahedron 49(10):1925 (1993) and references therein; Letsinger, J. Org. Chem. 35:3800 (1970); Sprinzl et al., Eur. J. Biochem.

81:579 (1977); Letsinger et al., Nucl. Acids Res. 14:3487 (1986); Sawai et al., Chem. Lett. 805 (1984), Letsinger et al., J. Am. Chem. Soc. 110:4470 (1988); and Pauwels et al., ChemicaScripta 26:141 (1986)), phosphorothioate (Mag et al., Nucleic Acids Res. 19:1437 (1991); and U.S. Pat. No. 5,644,048. Other nucleic analogs comprise phosphorodithioates (Briu et al., J. Am. Chem. Soc. 111:2321 (1989)), O-methylphosphoroamidite linkages (see Eckstein, Oligonucleotides and Analogues: A Practical Approach, Oxford University Press), those with positive backbones (Denpcy et al., Proc. Natl. Acad. Sci. USA 92:6097 (1995); non-ionic backbones (U.S. Pat. Nos. 5,386,023; 5,386,023; 5,637,684; 5,602,240; 5,216,141; and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (194): Chapters 2 and 3, ASC Symposium Series 580, "Carbohydrate Modifications in Antisense Research," Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research," Ed. Y. S. Sanghui and P. Dan Cook. Nucleic acids containing one or more carbocyclic sugars are also included within the definition of nucleic acids (see Jenkins et al., Chem. Soc. Rev. (1995) pp. 169-176). Several nucleic acid analogs are also described in Rawls, C & E News Jun. 2, 1997, page 35.

The term "universal nucleotide base" or "universal base," as used herein, refers to an aromatic ring moiety, which may or may not contain nitrogen atoms. In some embodiments, a universal base may be covalently attached to the C-1' carbon of a pentose sugar to make a universal nucleotide. In some embodiments, a universal nucleotide base does not hydrogen bond specifically with another nucleotide base. In some embodiments, a universal nucleotide base hydrogen bonds with nucleotide base, up to and including all nucleotide bases in a particular target polynucleotide. In some embodiments, a nucleotide base may interact with adjacent nucleotide bases on the same nucleic acid strand by hydrophobic stacking Universal nucleotides include, but are not limited to, deoxy-7-azaindole triphosphate (d7AITP), deoxyisocarbostyril triphosphate (dICSTP), deoxypropynylisocarbostyril triphosphate (dPICSTP), deoxymethyl-7-azaindole triphosphate (dM7AITP), deoxyImPy triphosphate (dImPyTP), deoxyPP triphosphate (dPPTP), or deoxypropynyl-7-azaindole triphosphate (dP7AITP). Further examples of such universal bases can be found, inter alia, in Published U.S. application Ser. No. 10/290,672, and U.S. Pat. No. 6,433,134.

As used herein, the terms "polynucleotide" and "oligonucleotide" are used interchangeably and mean single-stranded and double-stranded polymers of nucleotide monomers, including 2'-deoxyribonucleotides (DNA) and ribonucleotides (RNA) linked by internucleotidephosphodiester bond linkages, e.g., 3'-5' and 2'-5', inverted linkages, e.g., 3'-3' and 5'-5', branched structures, or internucleotide analogs. Polynucleotides have associated counter ions, such as $H^+$, $NH_4^+$, trialkylammonium, $Mg^{2+}$, $Na^+$, and the like. A polynucleotide may be composed entirely of deoxyribonucleotides, entirely of ribonucleotides, or chimeric compositions thereof. Polynucleotides may be comprised of internucleotide, nucleobase and/or sugar analogs. Polynucleotides typically range in size from a few monomeric units, e.g., 3-40 when they are more commonly frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytosine, "G" denotes deoxyguanosine, and "T" denotes thymidine, unless otherwise noted.

As used herein, "nucleobase" means those naturally occurring and those non-naturally occurring heterocyclic moieties commonly known to those who utilize nucleic acid technology or utilize peptide nucleic acid technology to thereby generate polymers that can sequence specifically bind to nucleic acids. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). Other non-limiting examples of suitable nucleobase include those nucleobases illustrated in FIGS. 2(A) and 2(B) of Buchardt et al. (WO92/20702 or WO92/20703).

As used herein, "nucleobase sequence" means any segment, or aggregate of two or more segments (e.g. the aggregate nucleobase sequence of two or more oligomer blocks), of a polymer that comprises nucleobase-containing subunits. Non-limiting examples of suitable polymers or polymers segments include oligodeoxynucleotides (e.g. DNA), oligoribonucleotides (e.g. RNA), peptide nucleic acids (PNA), PNA chimeras, PNA combination oligomers, nucleic acid analogs and/or nucleic acid mimics.

As used herein, "polynucleobase strand" means a complete single polymer strand comprising nucleobase subunits. For example, a single nucleic acid strand of a double stranded nucleic acid is a polynucleobase strand.

As used herein, "nucleic acid" is a nucleobase sequence-containing polymer, or polymer segment, having a backbone formed from nucleotides, or analogs thereof.

Preferred nucleic acids are DNA and RNA.

As used herein, nucleic acids may also refer to "peptide nucleic acid" or "PNA" means any oligomer or polymer segment (e.g., block oligomer) comprising two or more PNA subunits (residues), but not nucleic acid subunits (or analogs thereof), including, but not limited to, any of the oligomer or polymer segments referred to or claimed as peptide nucleic acids in U.S. Pat. Nos. 5,539,082; 5,527,675; 5,623,049; 5,714,331; 5,718,262; 5,736,336; 5,773,571; 5,766,855; 5,786,461; 5,837,459; 5,891,625; 5,972,610; 5,986,053; and 6,107,470; all of which are herein incorporated by reference. The term "peptide nucleic acid" or "PNA" shall also apply to any oligomer or polymer segment comprising two or more subunits of those nucleic acid mimics described in the following publications: Lagriffoul et al., Bioorganic & Medicinal Chemistry Letters, 4:1081-1082 (1994); Petersen et al., Bioorganic & Medicinal Chemistry Letters, 6:793-796 (1996); Diderichsen et al., Tett. Lett. 37:475-478 (1996); Fujii et al., Bioorg. Med. Chem. Lett. 7:637-627 (1997); Jordan et al., Bioorg. Med. Chem. Lett. 7:687-690 (1997); Krotz et al., Tett. Lett. 36:6941-6944 (1995); Lagriffoul et al., Bioorg. Med. Chem. Lett. 4:1081-1082 (1994); Diederichsen, U., Bioorganic & Medicinal Chemistry Letters, 7:1743-1746 (1997); Lowe et al., J. Chem. Soc. Perkin Trans. 1, (1997) 1:539-546; Lowe et al., J. Chem. Soc. Perkin Trans. 11:547-554 (1997); Lowe et al., J. Chem. Soc. Perkin Trans. 11:555-560 (1997); Howarth et al., J. Org. Chem. 62:5441-5450 (1997); Altmann, K-H et al., Bioorganic & Medicinal Chemistry Letters, 7:1119-1122

(1997); Diederichsen, U., Bioorganic & Med. Chem. Lett., 8:165-168 (1998); Diederichsen et al., Angew. Chem. Int. Ed., 37:302-305 (1998); Cantin et al., Tett. Lett., 38:4211-4214 (1997); Ciapetti et al., Tetrahedron, 53:1167-1176 (1997); Lagriffoule et al., Chem. Eur. J., 3:912-919 (1997); Kumar et al., Organic Letters 3(9):1269-1272 (2001); and the Peptide-Based Nucleic Acid Mimics (PENAMS) of Shah et al. as disclosed in WO96/04000.

The lipid nanoparticle of the invention differs from other similarly constituted materials by its morphology and characterized as having a substantially solid core. A lipid nanoparticle having a substantially solid core is a particle that does not have extended aqueous regions on the interior and that has an interior that is primarily lipid. In one embodiment, an extended region is a continuous aqueous region with a volume greater than half the particle volume. In a second embodiment, an extended aqueous region is more than 25% of the particle volume. The extent of internal aqueous regions may be determined by electron microscopy and appear as regions of low electron density. Further, because the interior of the solid core nanoparticle is primarily lipid, the aqueous content of the particle (the "trapped volume") per lipid constituting the particle is less than that expected for a unilamellar bilayer lipid vesicle with the same radius. In one embodiment, the trapped volume is less than 50% of that expected for a unilamellar bilayer vesicle with the same radius. In a second embodiment, the trapped volume is less than 25% of that expected for a unilamellar bilayer vesicle of the same size. In a third embodiment, the trapped volume is less than 20% of the total volume of the particle. In one embodiment, the trapped volume per lipid is less than 2 microliter per micromole lipid. In another embodiment the trapped volume is less than 1 microliter per micromole lipid. In addition, while the trapped volume per lipid increases substantially for a bilayer lipid vesicle as the radius of the vesicle is increased, the trapped volume per lipid does not increase substantially as the radius of solid core nanoparticles is increased. In one embodiment, the trapped volume per lipid increases by less than 50% as the mean size is increased from a diameter of 20 nm to a diameter of 100 nm. In a second embodiment, the trapped volume per lipid increases by less than 25% as the mean size is increased from a diameter of 20 nm to a diameter of 100 nm. The trapped volume can be measured employing a variety of techniques described in the literature. Because solid core systems contain lipid inside the particle, the total number of particles of a given radius generated per mole of lipid is less than expected for bilayer vesicle systems. The number of particles generated per mol of lipid can be measured by fluorescence techniques amongst others.

The lipid nanoparticles of the invention can also be characterized by electron microscopy. The particles of the invention having a substantially solid core have an electron dense core as seen by electron microscopy. Electron dense is defined such that area-averaged electron density of the interior 50% of the projected area of a solid core particle (as seen in a 2-D cryo EM image) is not less than x % (x=20%, 40%, 60%) of the maximum electron density at the periphery of the particle. Electron density is calculated as the absolute value of the difference in image intensity of the region of interest from the background intensity in a region containing no nanoparticle.

Therapeutic Material

As used herein, the term "therapeutic material" is defined as a substance intended to furnish pharmacological activity or to otherwise have direct effect in the diagnosis, cure, mitigation, treatment or prevention of disease, or to have direct effect in restoring, correcting or modifying physiological functions. Therapeutic materials include but are not limited to small molecule drugs, nucleic acids, proteins, peptides, polysaccharides, inorganic ions and radionuclides.

Research Reagent

As used herein, the term "research reagent" is defined as a substance intended to furnish a defined activity or to otherwise have direct influence on the biological effect of cells, tissues or organs. Research Reagents include but are not limited to small molecule organic compounds (e.g., organic compounds having molecular weights less than 800 g/mole, or less than 500 g/mole), nucleic acids, proteins, peptides, polysaccharides, inorganic ions and radionuclides. Examples of nucleic acid Research Reagents include but are not limited to antisense oligonucleotides, ribozymes, micro-RNA, mRNA, ribozyme, tRNA, snRNA, siRNA, shRNA, ncRNA, miRNA, mRNA, pre-condensed DNA, pDNA or an aptamer. Nucleic acid Research Reagents are used to silence genes (with for example siRNA), express genes (with for example mRNA), edit genomes (with for example CRISPR/Cas9).

Polymers

As used herein, the term "polymer" refers to compounds of usually high molecular weight built up chiefly or completely from a large number of similar units bonded together. Such polymers include any of numerous natural, synthetic and semi-synthetic polymers.

Natural Polymers

The term "natural polymer" refers to any number of polymer species derived from nature. Such polymers include, but are not limited to the polysaccharides, cellulose, chitin, and alginate.

Synthetic Polymers

The term "synthetic polymer" refers to any number of synthetic polymer species not found in nature. Such synthetic polymers include, but are not limited to, synthetic homopolymers and synthetic copolymers. Synthetic homopolymers include, but are not limited to, polyethylene glycol, polylactide, polyglycolide, polyacrylates, polymethacrylates, poly-ε-caprolactone, polyorthoesters, polyanhydrides, polylysine, and polyethyleneimine. "Synthetic copolymer" refers to any number of synthetic polymer species made up of two or more synthetic homopolymer subunits. Such synthetic copolymers include, but are not limited to, poly(lactide-co-glycolide), poly(lactide)-poly(ethylene glycol), poly(lactide-co-glycolide)-poly(ethylene glycol), and poly(ε-caprolactone)-poly(ethylene glycol).

Semi-Synthetic Polymers

The term "semi-synthetic polymer" refers to any number of polymers derived by the chemical or enzymatic treatment of natural polymers. Such polymers include, but are not limited to, carboxymethylcellulose, acetylated carboxymethylcellulose, cyclodextrin, chitosan, and gelatin.

Polymer Conjugate

As used herein, the term "polymer conjugate" refers to a compound prepared by covalently, or non-covalently conjugating one or more molecular species to a polymer. Such polymer conjugates include, but are not limited to, polymer-therapeutic material conjugates.

Polymer-Therapeutic Material Conjugate

As used herein, the term "polymer-therapeutic material conjugate" refers to a polymer conjugate where one or more of the conjugated molecular species is a therapeutic material. Such polymer-therapeutic material conjugates include, but are not limited to, polymer-drug conjugates.

Polymer-Drug Conjugate

As used herein, the term "polymer-drug conjugate" refers to any number of polymer species conjugated to any number of drug species. Such polymer drug conjugates include, but are not limited to, acetyl methylcellulose-polyethylene glycol-docetaxel.

As noted above, the nanoparticles of the invention are composed of particle-forming materials. Particle-forming materials include, among other components, lipids and polymers as described herein.

The following example is provided for the purpose of illustrating, not limiting, the invention.

Example

Materials 1,2-distearoyl-sn-glycero-3-phosphocholine (DSPC) was purchased from Avanti Polar Lipids (Alabaster, Ala., USA), cholesterol was obtained from Sigma (St Louis, Mo., USA), 1,17-bis(2-octylcyclopropyl)heptadecan-9-yl 4-(dimethylamino)butanoate (CL, for example, cationic lipid) was synthesized by Avanti Polar Lipids (Alabaster, Ala., USA), and polyethylene glycol-dimyristoyl propylamine (PEG-c-DMA) was synthesized by the Center for Drug Research and Development (Vancouver, BC, Canada). A 21-mer duplex siRNA was used for encapsulation in LNP systems.

Representative Preparation of siRNA-LNP Systems at Small Volumes

CL, DSPC, cholesterol, and PEG-lipid were first solubilized in ethanol at a molar ratio of 50:10:38.5:1.5 and total lipid concentration of 30.5 mg/mL to give the ethanol lipid solution. The siRNA was solubilized in a 25 mM acetate, pH=4.0 buffer at a concentration of 0.927 mg/mL to give the aqueous siRNA solution. A target siRNA/lipid ratio of 0.09 (wt/wt) was used. 40 µL of PBS was pipetted into the outlet well of the device. 30 µL of the aqueous siRNA solution was pipetted into the siRNA inlet well. 10 µL of the ethanol lipid solution was pipetted into the lipid inlet well. A manifold was then clamped over the inlet wells and pressurized using a Luer-lock syringe. Pressurization pushes the reagents in the inlet wells through the device and into the outlet wells, where they are immediately diluted at a ratio of 1:1 by the PBS that is preloaded in the outlet well. The sample volume of 80 µL is recovered by pipetting out of the outlet well and further diluted at a ratio of 1:1 with 80 µL of PBS.

The following protocol is with reference to FIGS. 3, 7, 9 and 10

Low Dead Volume Device Protocol (160 µL formulation)
1. Add 40 µL of dilution buffer (1×PBS) to the outlet port.
2. Add 30 µL of aqueous stock (with siRNA) to the inlet port marked "aqueous."
3. Add 10 µL of lipid stock to the inlet port marked "lipid."
4. Next, place the chip in the clamping device with the manifold on top of the chip, so that both the inlet ports are positioned inside the O-ring (place the manifold using bars on the clamping device as a guide to ensure the same).
5. Carefully lower the clamping block so that it sits on the manifold and push the lever towards the chip in order to secure the chip in place as well as seal the inlet ports within the O-ring of the manifold.
6. Fill a 3 mL syringe with about 2 mL of air and fix it onto the Luer lock port on the top side of the manifold.
7. Push the plunger rapidly.
8. Collect the formulation from the outlet port.
9. Add 80 µL of dilution buffer (1×PBS) to the formulation and pipette up and down a few times to ensure good mixing.

Washing the Device
1. Add 40 µL of distilled water and ethanol to the inlet ports marked "aqueous" and "lipid," respectively.
2. Fix the chip onto the manifold and pressurize with 2 mL of air. Remove the waste from the outlet port.
3. Repeat the above until the chip is clear and free of any deposits.
4. Push air through the chip (without any liquid) to expel of the remaining fluid inside the chip.
5. Blot out all three ports with a Kimwipe.
6. Leave the chip to dry at room temperature (takes around 1.5 to 2 hours).

The manufactured nanoparticles were cationic lipid: DSPC:Cholesterol:PEG-Lipid (50:10:38.5:1.5) encapsulating a 21-nucleotide duplex siRNA. The final volume of the nanoparticle solution was 160 µL.

Representative Preparation of mRNA-LNP Systems at Small Volumes

The process described above for siRNA-LNP systems can be adapted for preparation of mRNA-LNP. Essentially, the process is identical except that the mRNA was solubilized in a 75 mM acetate, pH=4.0 buffer and the (+/−) charge ratio, as expressed in the ratio of positive amino groups to negative phosphate groups, is increased from 3:1 to 8:1.

LNP Characterization.

Particle size was determined by dynamic light scattering using a Malvern Zetasizer NanoZS (Malvern Instruments, Westboro, Mass., USA). Intensity-weighted distribution data was used, and the average of two independent measurements was used for each sample. Encapsulation efficiency (% EE) was determined using the Quant-iT RiboGreen RNA Assay Kit (Life Technologies, Carlsbad, Calif., USA) from the ratio of fluorescence signal of the sample in the absence and presence of the LNP lysing detergent Triton X-100. Encapsulation efficiency was calculated using the formula:

$$\% EE = 1 - (F_{-Triton})/(F_{+Triton})$$

where:

$F_{-Triton}$=Fluorescence signal in the absence of Triton X-100

$F_{+Triton}$=Fluorescence signal in the presence of Triton X-100

All reported results are reported as the average of three (3) independent experiments.

Particle size, particle polydispersity, and percent of encapsulated active agent for the production of lipid nanoparticles prepared as described above using the device of FIG. 3 are summarized in Table 1.

TABLE 1

Lipid Nanoparticle Characteristics.

| Mixer Channel Width | Size (nm) | PDI | Encapsulation Efficiency |
|---|---|---|---|
| 200 µm | 94.1 | 0.11 | 90.60% |

In Vitro Testing of ZDV Formulations

Figure 11:
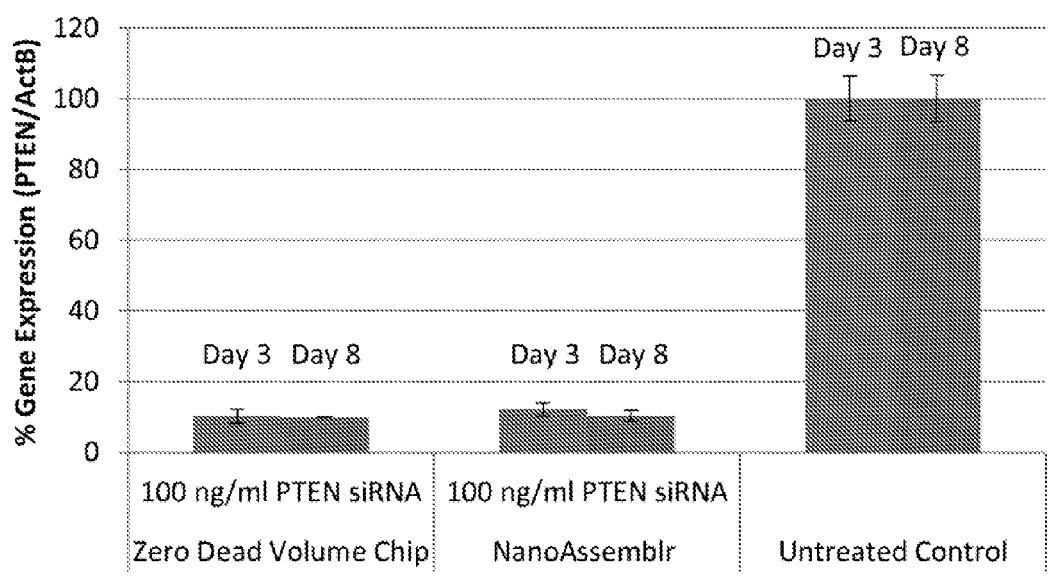
FIG. 11 compares PTEN Knockdown by siRNA-LNPs synthesized using NanoAssemblr and Zero Dead Volume Chip.

The siRNA-lipid nanoparticles (siRNA-LNPs) synthesized using a representative small volume microfluidic device of the invention (Zero Dead Volume Chip) were compared with those prepared using the NanoAssemblr (a fluidic device for making nanoparticles commercially available from Precision NanoSystems, Vancouver, British Columbia, Canada) by testing them in vitro on a rat E18 cortical neuron culture (co-cultured with glia and astrocytes). The cells were transfected on DIV 13 (days in vitro) at a dose of 100 ng of PTEN siRNA per ml of cell culture media. The knockdown of PTEN gene expression was then analysed at days 3 and 8 by RT-qPCR (with Actin β acting as a reference gene). The level of PTEN knockdown for both siRNA-LNP formulations was similar as shown in FIG. 11.

Figure 12:
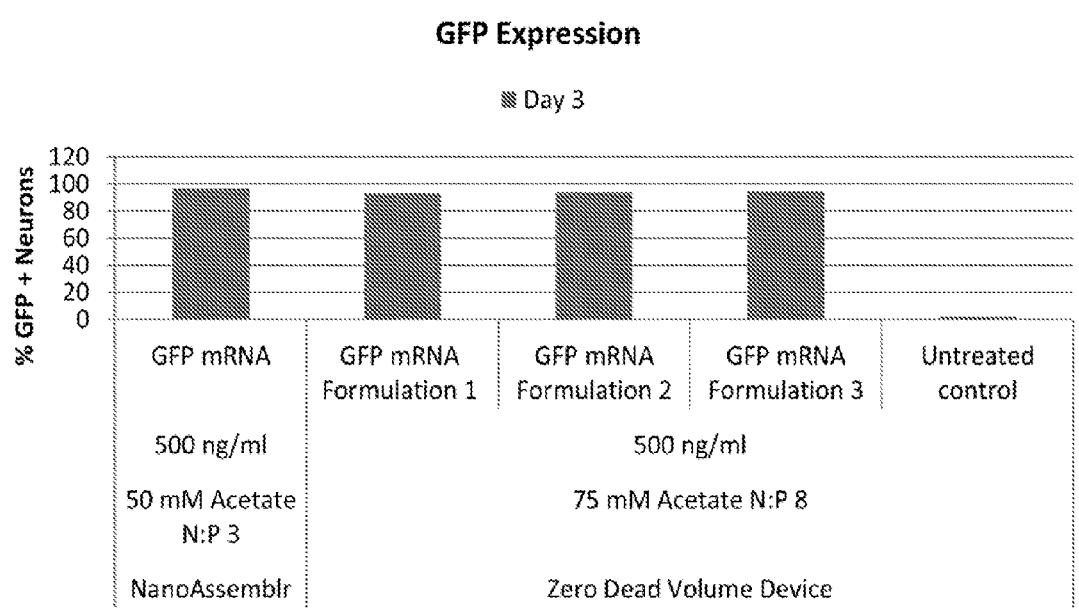
FIG. 12 compares levels of GFP expression on treatment with NanoAssemblr and Zero Dead Volume chip formulations.

The GFP mRNA-LNPs synthesized using the small volume microfluidic device (zero dead volume device) were compared with those prepared using the NanoAssemblr by testing them in vitro on a rat E18 cortical neuron culture (co-cultured with glia and astrocytes). The cells were transfected on DIV 13 (days in vitro) at a dose of 500 ng of GFP mRNA per ml of cell culture media. The expression of GFP was analyzed on day 3 by flow cytometry. The levels GFP expression for both the NanoAssemblr and Zero Dead Volume Chip mRNA-LNP formulations were observed to be similar as can be seen in FIG. 12.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A device, comprising:
   (a) a first well for receiving a first solution comprising a first solvent;
   (b) a first channel having a first impedance in fluid communication with the first well;
   (c) a second well for receiving a second solution comprising a second solvent;
   (d) a second channel having a second impedance in fluid communication with the second well;
   (e) a third channel for receiving first and second streams flowed from the first and second wells through the first and second channels, respectively, wherein the third channel has a first region adapted for flowing the first and second streams introduced into the channel and a second region adapted for mixing the contents of the first and second streams to provide a third stream; and
   (f) a third well for receiving the third stream, wherein the third well is configured to provide, when filled with a third solution, a backpressure in the third channel that will stop fluidic movement from the first well and the second well until a forward pressure is applied to the first well and the second well;
   wherein the first impedance is different than the second impedance, resulting in different flow rates through the first channel and the second channel.

2. The device of claim 1, further comprising a valve configured to stop fluidic movement to the third well.

3. The device of claim 1, wherein the difference between the first impedance and the second impedance results from a difference in a property of the first channel and the second channel selected from the group consisting of channel length, channel height, channel width, channel surface, and combinations thereof.

4. The device of claim 1, wherein a ratio of the first impedance to the second impedance is from 2.5:1 to 3:1.

5. The device of claim 4, wherein the ratio of the first impedance to the second impedance results from the first channel having a different length than the second channel.

6. The device of claim 1, wherein the second region of the third microchannel has a hydrodynamic diameter of about 20 microns to about 400 microns.

7. The device of claim 1, wherein the second region of the third microchannel comprises a micromixer.

8. The device of claim 1, wherein the second region of the third microchannel comprises a chaotic advection micromixer.

9. The device of claim 1, wherein the second region of the third microchannel comprises bas-relief structures.

10. The device of claim 9, wherein the bas-relief structures comprise a plurality of herringbone bas-relief structures.

11. The device of claim 1, wherein the second region of the third microchannel has a principal flow direction and one or more surfaces having at least one groove or protrusion defined therein, the at least one groove or protrusion having an orientation that forms an angle with the principal direction.

12. The device of claim 1, further comprising a pressure manifold configured to form a sealed connection between a source of pressure and the first inlet and the second inlet, such that the same pressure can be delivered to the first inlet and the second inlet.

13. The device of claim 12, further comprising a clamping device configured to maintain the sealed connection between the first inlet, the second inlet, and the pressure manifold.

14. The device of claim 12, wherein the source of pressure comprises a syringe configured to form a sealed connection with the pressure manifold.

* * * * *